(12) United States Patent
Crawford et al.

(10) Patent No.: US 6,348,639 B1
(45) Date of Patent: *Feb. 19, 2002

(54) BIOLOGICAL SYSTEM FOR DEGRADING NITROAROMATICS IN WATER AND SOILS

(75) Inventors: Donald L. Crawford, Moscow, ID (US); Todd O. Stevens, Mosier, OR (US); Ronald L. Crawford, Moscow, ID (US)

(73) Assignee: Idaho Research Foundation, Inc., Moscow, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/588,439

(22) Filed: Jun. 6, 2000

Related U.S. Application Data

(63) Continuation of application No. 08/799,577, filed on Feb. 12, 1997, now Pat. No. 6,084,150, which is a continuation of application No. 08/545,903, filed on Oct. 20, 1995, now Pat. No. 5,616,162, which is a continuation of application No. 08/229,413, filed on Apr. 18, 1994, now Pat. No. 5,455,173, which is a continuation of application No. 08/729,462, filed on Apr. 18, 1994, now abandoned, which is a continuation of application No. 08/096,735, filed on Jul. 23, 1993, now Pat. No. 5,387,271, which is a continuation of application No. 07/508,056, filed on Apr. 11, 1990, now abandoned.

(51) Int. Cl.⁷ ............................. A62D 3/00; B09B 3/00; C09K 17/00
(52) U.S. Cl. ..................... 588/244; 435/262.5; 405/263
(58) Field of Search ................................. 588/244, 205; 435/262.5, 167, 262; 405/263; 210/603, 610, 611; 71/6, 8, 9, 10, 903, 904

(56) References Cited

U.S. PATENT DOCUMENTS 4,826,601 A    5/1989   Spratt et al.
4,919,813 A    4/1990   Weaver
4,925,552 A    5/1990   Bateson et al.

(List continued on next page.)

FOREIGN PATENT DOCUMENTS

DE    3818398 A1    12/1989
EP    0 251 320 A2  1/1988
NL    8602985       6/1988

(List continued on next page.)

OTHER PUBLICATIONS

Gorontzy et al., "Microbial transformation of nitroaromatic compounds under anaerobic conditions," *J. Gen. Microbiol.* 139:1331–1336, 1993.

(List continued on next page.)

*Primary Examiner*—Steven P. Griffin
*Assistant Examiner*—Eileen E. Nave
(74) *Attorney, Agent, or Firm*—Klarquist & Sparkman, LLP

(57) ABSTRACT

Methods for biodegrading nitroaromatic compounds present as contaminants in soil or water using microorganisms are disclosed. Water is treatable directly; dry soil is first converted into a fluid medium by addition of water. The preferred method comprises two stages, each employing microorganisms: a fermentative stage, followed by an anaerobic stage. The fermentative stage is rapid, wherein an inoculum of aerobic and/or facultative microorganisms ferments a carbohydrate added to the fluid medium, exhausting the oxygen in the fluid medium and thereby inhibiting oxidative polymerization of amino by-products of the nitroaromatics. In the subsequent anaerobic stage, an inoculum of a mixed population of anaerobic microorganisms completes the mineralization of the contaminant nitroaromatics, using the remaining carbohydrate as a carbon and energy source. Preferably, the carbohydrate is a starch and the aerobic and/or facultative microorganisms are amylolytic, which cleave the starch at a moderate rate throughout both stages, ensuring a sustained supply of metabolizable carbohydrate. The microorganisms are preferably selected to be resistant to the types and concentrations of nitroaromatics present as contaminants.

20 Claims, 10 Drawing Sheets

U.S. PATENT DOCUMENTS

| | | | |
|---|---|---|---|
| 4,968,427 A | 11/1990 | Glanser et al. | |
| 5,062,956 A | 11/1991 | Lupton et al. | |
| 5,071,755 A | 12/1991 | Nelson et al. | |

FOREIGN PATENT DOCUMENTS

| | | |
|---|---|---|
| WO | WO 91/15440 | 4/1991 |
| WO | WO 95/01311 | 7/1994 |
| WO | WO 95/03259 | 7/1994 |

OTHER PUBLICATIONS

McBride et al., "Metabolism of the herbicide bromoxynil by *Klebsiella pneumoniae* subsp. *ozaenae*," *Appl. Environ. Microbiol.* 52:325–330, 1986.

Preuss et al., "Anaerobic transformation of 2, 4, 6–trinitrotoluen 9TNT," *Arch. Microbiol.* 159:345–353, 1993.

Pumfrey and Roberts, "A Clostridium species that grows on 2, 4, 6–trinitrotoleune (TNT)," (Abstract), *Abstr. Gen. Meet. Am. Soc. Microbiol.*, 1993.

Rafii et al., "Reduction of nitroaromatic compounds by anerobic bacteria isolated from the human gastrointestinal tract," *Appl. Environ. Microbiol.*, 57:962–968, 1991.

Rafii and Cerniglia, "Reduction of azo dyes and nitroaromatic compounds by the same extracellular enzyme from *clostridium perfringens*," (Abstract), *Abstr. Gen. Meet. Am. Soc. Microbiol.*, 1993.

Chemical Abstracts 92(16), 1980, Abstract No. 134719. [Abstract of Yang et al., "Bacteria transforming 2, 4, 6–trinitrotoluene and their application," *Wei Sheng Wu Hsueh Pao* 19:408–415, 1979].

Zewald et al., "Biodegradatie Als Bodemsaneringstechniek," *PT/Civiele Techniek*, 39:7–15 (1984).

Tiedhe and Stevens, "The Ecology of an Anaerobic Dechlorinating Consortium," in Omenn (ed.) *Environmental Biotechnology*, pp. 2–14 (1988).

Hallas et al., "Microbial Transformation of Nitroaromatic Compounds in Sewage Effluent," *Appl. Environ. Microbiol.*, 45:1234–41 (1983).

Channon et al., "The Metabolism of 2:4:6–Trinitrotuluene (α–T.N.T.)," *Biochem. J.*, 38:70–85 (1944).

Zeyer et al., "Degradation of o–Nitrophenol and m–Nitrophenol by a *Pseudomonas putida*," *J. Agric. Food Chem.*, 32:238–242 (1984).

Simmons et al., "Oxidative Co–Oligomerization of Guaiacol and 4–Chloroaniline," *Environ. Sci. Technol.*, 23:115–121 (1989).

Cartwright et al., "Bacterial Degradation of the Nitrobenzoic Acids," *Biochem. J.*, 71:248–261 (1958).

Kaplan, "Biotransformation Pathways of Hazardous Energetic Organo–Nitro Compounds," in Kamely, D. et al. (eds.), *Biotechnology and Biodegradation, Gulf Pub. Co.*, pp. 155–180 (1990).

Naumova et al., Possibility of Deep Bacterial Destruction of 2, 4, 6–Trinitrotoluene, *MikrobiologiyaI*, 57:218–222 (1988).

Schink, "Principles and Limits of Anaerobic Degradation: Environmental and Technological Aspects," in Zinder (ed.), *Biology of Anaerobic Microorganisms*, Wiley, NY, pp. 771–846 (1988).

McCormick et al., Microbial Transformation of 2, 4, 6–Trinitrotoluene and Other Nitroaromatic Compounds, *Appl. Environ. Microbiol.*, 31:949–958 (1976).

Tschech et al., "Methanogenic Degradation of Anthranilate (2–Aminobenzoate)," *System. Appl. Microbiol.*, 11:9–12 (1988).

Doyle et al., "Effect of Dairy Manure and Sewage Sludge on [14–C]—Pesticide Degradation in Soil," *J. Agric. Food Chem.*, 26:987–989 (1978).

Spain et al., "Enzymatic Oxidation of p–Nitrophenol," *Biochem. and Biophys. Research Communications*, 88:634–641 (1979).

Jensen et al., "Microorganisms that Decompose Nitro–Aromatic Compounds, With Special Reference to Dinitro–Ortho–Cresol," *Acta Agriculturae Scandinavica*, 17:115–126 (1967).

Berry et al., "Microbial Metabolism of Homocyclic and Heterocyclic Aromatic Compounds Under Anaerobic Conditions," *Microbiol. Rev.*, 51:43–59 (1987).

Parris, "Environmental and Metabolic Transformations of Primary Aromatic Amines and Related Compounds," *Residue Reviews*, 76:1–30 (1980).

Wallnöfer et al., Transformation of Dinitrophenol–Herbicides by Azotobacter Sp., *Chemosphere*, 12:967–972 (1978).

Ziegler et al., "Activation of Aromatic Acids and Aerobic 2–Aminobenzoate Metablolism in a Denitrifying Pseudomonas Strain," *Arch. Microbiol.*, 151:171–176 (1989).

Ziegler et al., "Studies on the Anaerobic Degradation of Benzoic Acid and 2–Aminobenzoic Acid by a Denitrifying Pseudomonas Strain," *Arch. Microbiol.*, 149:62–69 (1987).

Smolenski et al., "Biodegradation of Cresol Isomers in Anoxic Aquifers," *Appl. Environ. Microbiol.*, 53:710–716 (1987).

Kuhn et al., "Anaerobic Degradation of Alkylated Benzenes in Denitrifying Laboratory Aquifer Columns," *Appl Environ. Microbiol.*, 54:490–496 (1988).

Fröslie et al., "Ruminal Metabolism of DNOC and DNBP," *Acta Vet. Scand.*, 11:114–132 (1970).

Tratnyek et al., "Abiotic Reduction of Nitro Aromatic Pesticides in Anaerobic Laboratory Systems," *J. Agric. Food Chem.*, 37:248–254 (1989).

Vlassak et al., "Dinoseb as a Specific Inhibitor of Nitrogen Fixation in Soil," *Soil Biol. Biochem.*, 8:91–93 (1976).

Federle, "Mineralization of Monosubstituted Aromatic Compounds in Unsaturated and Saturated Subsurface Soils," *Can. J. Microbiol.*, 34:1037–1042 (1988).

Braun et al., "Anaerobic Degradation of 2–Aminobenzoate (Anthranilic Acid) by Denitrifying Bacteria," *Appl. Environ. Microbiol.*, 48:102–107 (1984).

Kaplan et al., "Thermophilic Biotransformations of 2, 4, 6–Trinitrotoluene Under Simulated Composting Conditions," *Appl. Environ. Microbiol.*, 44:757–760 (1982).

Stevens, "Biodegradation of Dinoseb (2–sec–Butyl–4, 6–Dinitrophenol) and Bioremediation of Dinoseb–Contaminated Soils," Ph.D. Thesis, University of Idaho (1989).

BIOLOGICAL SYSTEM FOR DEGRADING NITROAROMATICS IN WATER AND SOILS

CROSS-REFERENCE TO RELATED APPLICATIONS

This application is a continuation U.S. patent application Ser. No. 08/799,577, filed on Feb. 12, 1997 which issued as U.S. Pat. No. 6,084,150; which is a continuation of U.S. patent application Ser. No. 08/545,903, filed on Oct. 20, 1995, which issued as U.S. Pat. No. 5,616,162; which is a continuation of U.S. patent application Ser. No. 08/229,413, filed on Apr. 18, 1994, which issued as U.S. Pat. No. 5,455,173; which is a continuation of U.S. patent application Ser. No. 08/096,735, filed on Jul. 23, 1993, which issued as U.S. Pat. No. 5,387,271; which is a file-wrapper, continuation of U.S. patent application Ser. No. 07/508,056 filed Apr. 11, 1990, now abandoned. The present application is equivalent to a continuation of application Ser. No. 07/508,056, now abandoned.

FIELD

This invention relates to the biodegradation of various nitroaromatic compounds in water and soils, including dinoseb (2-(1-methylpropyl)-4,6-dinitrophenol), using microorganisms.

BACKGROUND

Certain nitrophenolic compounds are sufficiently toxic to life to render them effective for use as herbicides, insecticides, or miticides. Such compounds include dinoseb (2-(1-methylpropyl)-4,6-dinitrophenol) which has been widely used as a herbicide since the 1950's on a variety of crops in the United States. Concerns for the safety of agricultural workers has resulted in discontinued use of dinoseb. However, numerous sites remain contaminated with this compound.

Other nitroaromatic compounds are similar to dinoseb in terms of chemical structure, but have other applications, such as in explosives. Such compounds include trinitrotoluene (TNT) and dinitrotoluene (DNT). Because of the widespread use of these compounds over a lengthy period of time, many sites have become contaminated with these compounds, including both manufacturing and military sites.

Many nitroaromatic compounds are either poorly degradable or nondegradable in field environments outside the laboratory. Previously, land farming was the favored method for disposing of these and other chemicals, wherein the chemicals were mixed with soil, fertilizer was added, and the mixture aerated to promote microbial activity. Unfortunately, nitroaromatics were not satisfactorily degraded by land farming or other well-aerated processes. Possible reasons include lack of nitroaromatic-degrading microorganisms, partitioning of the contaminant chemicals to biologically sequestered or inhospitable parts of the environment, and accumulation of toxic partial-breakdown by-products. Problems with land farming in general included the slow rate of biodegradation, high expense, and accumulation of toxic by-products.

Other methods have been used to remove nitroaromatics and similar compounds from contaminated soils, but with little practical success. Such methods include transportation of contaminated soil to hazardous waste dumps, and on-site incineration of the soil. Problems with such methods include high cost and poor accountability of the responsible party.

Previous laboratory studies indicated that certain nitroaromatic molecules are susceptible at least to microbiological transformation. However, the studies did not disclose biochemical mechanisms of such transformation or degradation or whether the nitroaromatic compounds were completely mineralized. In one study, for example, a soil Moraxella microorganism was isolated that was capable of growth on p-nitrophenol as its only source of carbon and energy. Spain et al., *Biochem. Biophys. Res. Comm.* 88:634–641 (1959). In another study, the anaerobic bacteria *Veillonella alkalescens* reductively transformed nitroaromatic compounds, converting the nitro groups to amino groups. McCormack et al., *Appl. Environ. Microbiol.* 31:949–958 (1976).

Aminoaromatic derivatives of nitroaromatics can undergo enzymatic oxidation to form polymeric (large molecular weight) materials. Parris, *Residue Revs.* 76:1–30 (1980). In the field, such polymers are usually incorporated into soil humic matter. Channon et al., *Biochem. J.* 38:70–85 (1944); McCormick et al., *Appl. Environ. Microbiol.* 31:949–958 (1976); Simmons et al., *Environ. Sci. Technol.* 23:115–121 (1989). Humic matter tends to be long-lived in soils, thereby representing a major long-term environmental fate of many nitroaromatics and aminoaromatics. Other soil microorganisms are capable of cleaving the azo linkages of polymerized aminoaromatics, often forming toxic by-products.

Bacteria are also able to attack nitrobenzoic acid, Cartwright and Cain, *Biochem. J.* 71:248–261 (1959), as well as o-nitrophenol and m-nitrophenol, Zeyer and Kearney, *J. Agric. Food Chem.* 32:238–242 (1984), where the nitro group is released as nitrite. Again, however, complete mineralization has not been demonstrated. Further, nitrite release has not been found to be a significant pathway for highly substituted nitroaromatics. No instance is currently known where a compound possessing more than one nitro substituent has been completely mineralized. In fact, the pertinent literature presents no evidence supporting ring cleavage of highly substituted nitroaromatics. Kaplan, "Biotransformation Pathways of Hazardous Energetic Organo-Nitro Compounds," in *Biotechnology and Degradation. Adv. Appl. Biotechnol. Ser.* 4:155–181, Gulf Pub. Co., Houston, Tex. (1990).

Aromatic groups in general appear to be degradable via only a few aerobic and anaerobic pathways. Gottschalk, *Bacterial Metabolism,* 2d ed., Springer Verlag, New York (1986), pp. 157–162; Berry et al., *Microbiol. Rev.* 51:43–59 (1987); Schink, "Principles and Limits of Anaerobic Degradation: Environmental and Technological Aspects," in Zinder (ed.), *Biology of Anaerobic Microorganisms*, Wiley, New York (1988). Aerobically, many aromatic groups are degraded to catechol, protocatechuate or homogentisate by the action of oxygenase and dioxygenase enzymes. Catechol and protocatechuate can be degraded further by aromatic ring cleavage either ortho or meta to the hydroxyl groups. Because of the difficulty of working with anaerobic microorganisms and processes, biochemical pathways describing anaerobic degradation of aromatic compounds have been less well characterized.

Alkyl groups on aromatic rings are degradable via reactions similar to those for simple alkanes. Under aerobic conditions, the terminal carbon is oxidized to yield a carboxylic acid. Degradation then proceeds by $\beta$-cleavage to yield either benzoates (odd-numbered carbon chains) or phenylacetates (even-numbered carbon chains). No anaerobic microorganisms capable of carrying out this process have been isolated to date. In spite of the above results known in the art, there is little information currently available on practical means of using microbial cultures to bioremediate nitroaromatic-contaminated soils.

Dinoseb, an intensely yellow-colored compound visible at concentrations as low as 10 ppm, has been found to not significantly accumulate in agricultural soil at normal application rates, even after years of repeated application. Doyle et al., *J. Agric. Food Chem.* 26:987–989 (1978). However, higher application rates, such as from spills of substantial amounts of the compound, can result in appreciable accumulation at a site. Presumably, therefore, dinoseb at lower concentrations is transformed by certain soil microorganisms. Such transformation appears to result only in the formation of amino and acetoamido forms of dinoseb, which apparently retain significant toxicity. Parris, *Residue Revs.* 76:1–30 (1980).

Previous work on the biotransformation of the explosive 2,4,6-trinitrotoluene (TNT) indicates that the primary mode involves transformation (reduction) of the nitro groups. Kaplan, supra. A recent paper from Soviet researchers describes degradation of TNT by a strain of *Pseudomonas fluorescens*. Naumova et al., *Mikrobiologiya* 57:218 (1988). But, while these reports shed some light on microbial events and hypothetical biochemical mechanisms therefor, they neither disclose nor suggest effective methods for bioremediating soils or wastewater contaminated with these compounds. Further, the Soviet results have not been confirmed outside the U.S.S.R.

Hence, although several anaerobic microbiological systems have been described for degrading other aromatic chemicals, little to no information is available on practical means of using these cultures to bioremediate contaminated soils and waters, especially soils and waters contaminated with nitroaromatics. In today's world, effective remediation of environmental sites contaminated with compounds, such as nitroaromatics, requires that the contaminants be completely mineralized to ensure the absence of latently toxic by-products. Such results for nitroaromatics simply have not been shown in the prior art, particularly as applicable to large-scale, low-cost bioremediation efforts.

Therefore, there remains a need for a method to effectively bioremediate dinoseb-contaminated soils, as well as soils contaminated with other nitroaromatic compounds, such as TNT and DNT.

Further, there is a need for such a method that can be performed at a natural site contaminated with dinoseb or a related nitroaromatic compound.

Further, there is a need for such a method that can completely degrade dinoseb and other nitroaromatics, leaving no detectable or environmentally significant amounts of aromatic by-products or other toxic intermediary compounds, including polymeric derivatives.

Further, there is a need for such a method employing microorganisms of types and species profiles normally found in many soil environments.

Further, there is a need for such a method that is inexpensive and easy to perform, particularly on a large-scale, in the field.

Further, there is a need for such a method that can be performed rapidly, including in the field.

Further, there is a need for such a method that will effect bioremediation of nitroaromatic-contaminated soil without specialized bioreactors or other complex equipment.

SUMMARY

In accordance with the present invention, soil or water contaminated with one or more nitroaromatic compounds is subjected to a two-stage bioremediation process employing different microorganisms during each stage. The stages comprise an initial fermentation stage followed by an anaerobic stage. Most of the actual biodegradation of the contaminant nitroaromatics takes place in the anaerobic stage. At the end of the anaerobic stage, the contaminant nitroaromatics have been biodegraded to non-toxic end products.

As another aspect of the invention, complete biodegradation of nitroaromatics has been found to occur only under anaerobic conditions. Since anaerobiosis generally requires an aqueous environment, it is usually necessary to add extraneous water to a nitroaromatic-contaminated soil to create a fluid mud slurry of the soil before beginning the process. Contaminated water can be subjected to the process directly.

During the first stage of the process, the normally aerobic contaminated soil (with water added to form a mud slurry) or contaminated water alone is rendered anaerobic. The preferred method for achieving an anaerobic condition is by a fermentation of a supply of starchy carbohydrate or other readily fermentable carbon source added to the slurry or water. Fermentation, where the carbon source is a starchy carbohydrate, is performed by one or more species of aerobic or facultatively anaerobic amylolytic microorganisms inoculated into the slurry or water. Amylolytic microorganisms are not required if the carbon source is a simple sugar, such as fructose or glucose.

As another aspect of the invention, the aerobic or facultative microorganisms are preferably isolated and enriched in a culture containing the particular nitroaromatic present in the contaminated soil or water.

As another aspect of the invention, it is usually necessary at the beginning of the aerobic stage to add an extraneous source of nitrogen for the microorganisms. The nitrogen source is preferably in the form of ammonium ion or simple amino compounds readily utilizable by aerobic and anaerobic microorganisms.

As another aspect of the invention, it is preferable to stimulate a rapid onset of intense fermentation to quickly cause exhaustion of the oxygen dissolved in the slurry or water, thereby rendering the slurry or water anaerobic, without exhausting the carbon source. Quick attainment of anaerobiosis minimizes oxidative polymerization of any amino derivatives of the nitroaromatics that tend to form under aerobic conditions. Once formed, such polymers are difficult to biodegrade. Rapid anaerobiosis can be achieved by inoculating the slurry or water with a large dosage of aerobic and/or facultative fermentative microorganisms.

If necessary, mineral nutrients, including phosphate salts, can be added to the soil slurry or water to facilitate microbial growth. Supplementary vitamins and cofactors may also be required, but probably only when treating wastewaters having very little dissolved organic carbon. Soils generally have sufficient nutrients.

As another aspect of the invention, the carbon source added to the soil slurry or water for aerobic fermentation is preferably a starchy carbohydrate substance hydrolyzable to constituent sugars by amylolytic microorganisms in the aerobic inoculum. A starch is preferred over merely adding free sugar because the starch serves as a reservoir of metabolizable carbohydrate that ensures an adequate supply of easily metabolizable sugar for the microorganisms, both in the aerobic stage and in the anaerobic stage. Anaerobic biodegradation of nitroaromatics requires such a sustained sugar supply. A supply of sugar added at the beginning of the aerobic stage would generally be exhausted prematurely, making it difficult to maintain anaerobic conditions for the requisite amount of time to achieve complete mineralization of the nitroaromatics.

As another aspect of the invention, the amount of starchy carbohydrate to be added to the volume of soil slurry or water to be treated can be "tailored" to ensure the desired degree of biodegradation is attained and waste of carbohydrate is avoided. The amount of carbohydrate should be just sufficient to supply the metabolic needs of the microorganisms until the anaerobic biodegradation of contaminant nitroaromatics is complete.

As yet another aspect of the invention, once strict anaerobic conditions have been attained in the volume of slurry or water, an inoculum comprised of an anaerobic consortium of microorganisms is added to the volume to start the second, or anaerobic, stage. Anaerobic conditions are preferably determined via a potentiometric measurement, where a redox potential of –200 mV or less indicates strict anaerobic conditions.

As yet another aspect of the invention, the anaerobic consortium comprises multiple species of microorganisms that have been grown in a medium containing one or more nitroaromatics identical or similar to the contaminant nitroaromatics to be biodegraded. The anaerobic microorganisms are able to biodegrade the nitroaromatics in the presence of metabolizable sugar to simple non-toxic compounds, such as methane, carbon dioxide, and acetate.

As yet another aspect of the invention, after inoculation, the anaerobic consortium is afforded sufficient time to biodegrade the contaminant nitroaromatics in the soil slurry or water to non-toxic end-products. Because degradation of the nitroaromatic compounds occurs in an anaerobic environment, polymerization to toxic humic-like compounds and other large, long-lived, latently toxic molecules normally formed in aerobic environments is prevented.

As yet another aspect of the invention, the present method is preferably performed in a suitably large covered vessel for containing the contaminated soil slurry or water during bioremediation. Such containment ensures that anaerobic conditions in the soil slurry or water are reached more rapidly and are better controlled and maintained. Containment also facilitates easier control of environmental parameters, such as temperature, pH, and, if needed, escape of volatile gases from the slurry or water being treated.

It is accordingly one object of the present invention to provide a method for effectively bioremediating soils and waters contaminated with one or more nitroaromatic compounds.

Another object of the present invention is to provide such a method that can be performed at natural sites contaminated with nitroaromatics.

Another object of the present invention is to provide such a method that will allow contaminant nitroaromatics in soil or water to be biodegraded to such an extent that no detectable or environmentally significant amounts of aromatic by-products or other toxic intermediary compounds are left in the soil or water, including latently toxic polymeric derivatives of the nitroaromatics.

Another object of the present invention is to provide such a method that utilizes microorganisms similar to those found in many soil and aquatic environments.

Another object is to provide such a method that is inexpensive and easy to perform, particularly on a large scale in the field.

Another object is to provide such a method that can be performed rapidly, even in the field.

These and other objects, features, and advantages of the present invention will become apparent with reference to the following description and drawing.

BRIEF DESCRIPTION OF THE DRAWINGS

The drawing consists of multiple figures, in which.

DETAILED DESCRIPTION

Selection and Isolation of Dinoseb-Degrading Microorganisms

Figure 1:
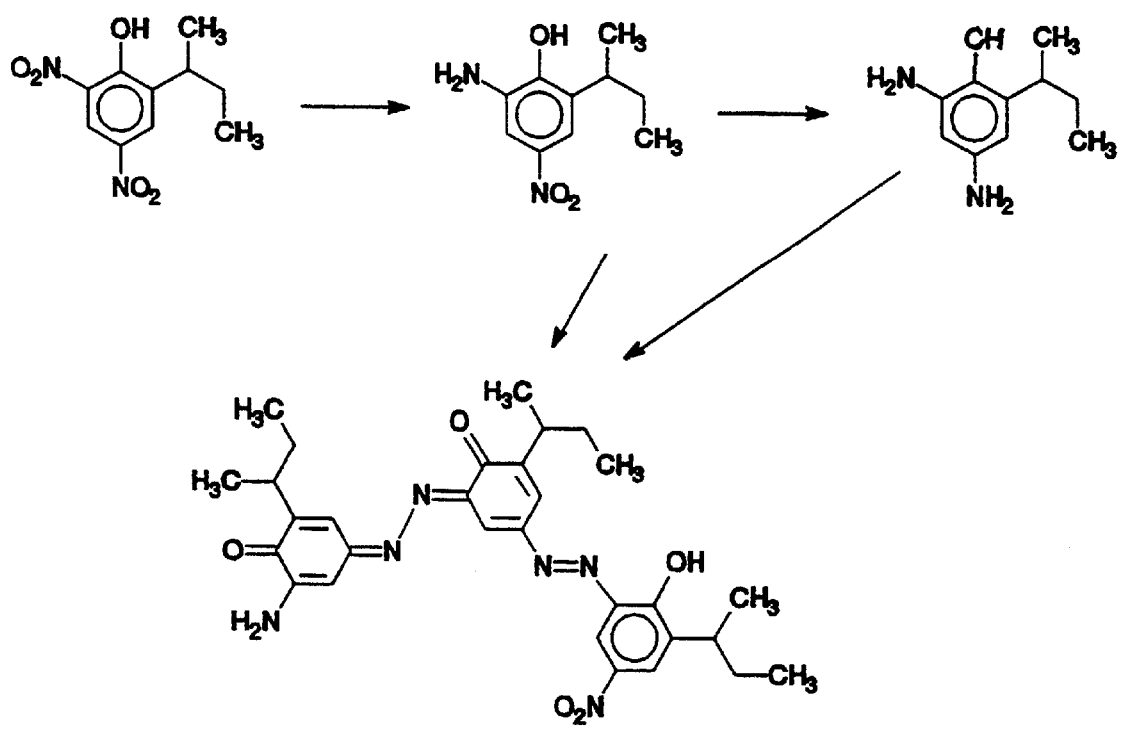
FIG. 1 is a schematic depiction of the formation of an amino derivative of the representative nitroaromatic compound "dinoseb" under aerobic conditions and the subsequent aerobic polymerization of amino derivatives into undesirable humic-like compounds retaining the latent toxicity of dinoseb.

Various microorganisms capable of at least transforming dinoseb were preliminarily selected and enriched using a chemostat having a 1-L capacity vessel and agitation capability (Series 500 Fermenter, L. H. Fermentation, Hayward, Calif.). An approximately 250 mL volume of 3 mm diameter glass beads were placed in the bottom of the chemostat vessel to act as a soil-holding matrix. As a result, both aerated (supernatant liquid) and non-aerated (soil sediment) enrichment conditions were simultaneously maintained in the chemostat.

As used herein, "transformation" of dinoseb or other nitroaromatic compound means a chemical change other than degradation. The simplest way to confirm transformation of dinoseb is to observe the disappearance of the bright yellow color of the compound. Under aerobic conditions, dinoseb is transformed into an amino form that subsequently becomes polymerized by oxidative coupling. The term "degradation" denotes the complete mineralization of the subject nitroaromatic to ethane, carbon dioxide, and acetate.

To provide a source of mineral nutrients to the microorganisms in the chemostat, a mineral nutrient solution was prepared containing the following solutes: $KH_2PO_4$ (272 mg/L), $K_2HPO_4$ (348 mg/L), $Na_2SO_4$ (5 mg/L), $MgSO_4.7H_2O$ (5 mg/L), $CaCl_2.2H_2O$ (1 mg/L), and $FeSO_4$ (0.5 mg/L). The nutrient solution was supplemented with selected carbon and nitrogen sources, as discussed further below, in an attempt to effect a satisfactory preliminary selection of dinoseb-degrading microorganisms. The initial inoculum of microorganisms consisted of indigenous microbes associated with a 200-gram sample of a soil mixture removed from a site previously exposed to dinoseb and suspected of having dinoseb-degrading activity. The chemostat was operated at a flow rate of 10 mL/hr, pH 7, and 25° C. Carbon and nitrogen sources for the microorganisms used individually in separate attempts at selection included: 50 ppm dinoseb plus 50 ppm 2,4-dinitrophenol, 50 ppm dinoseb plus 50 ppm 2,4-dinitrophenol plus 1 g/L $NH_4Cl$, 50 ppm dinoseb plus 50 ppm phenol, and 100 ppm dinoseb plus 0.5 g/L glucose and 1 g/L $NH_4Cl$.

No dinoseb degradation or turbidity occurred in the chemostat during thirty days' incubation and agitation with 50 ppm dinoseb plus 50 ppm 2,4-dinitrophenol as the sole carbon substrate. When the chemostat was operated for another thirty days with 50 ppm dinoseb plus 50 ppm 2,4-dinitrophenol and 1 g/L $NH_4Cl$, no dinoseb degradation or turbidity resulted. When the chemostat was operated for forty-two days with 50 ppm dinoseb, 50 ppm 2,4-dinitrophenol, and 50 ppm phenol, no dinoseb degradation occurred, but turbidity did develop. Most importantly, when the chemostat was operated with 0.5 g/L glucose, 100 ppm dinoseb, and 1 g/L $NH_4Cl$, turbidity developed immediately and dinoseb degradation began after twenty days. The latter result indicated that, to effect degradation of dinoseb by either aerobic or anaerobic processes, supplementary glucose is required as a carbon source. Continuing with the latter operational conditions, the flow rate was then increased to 20 mL/hr for another thirty days to complete the preliminary selection process.

After preliminary selection, samples of the supernatant liquid presumed to contain various aerobic and/or facultative microorganisms were removed from the chemostat and plated on nutrient agar to obtain a number of isolates of specific microorganisms. The isolates were then cultured under aerobic, anaerobic, and microaerophilic conditions wherein their individual abilities to transform or degrade dinoseb were evaluated. For aerobic culturing, the mineral nutrient solution described above was used, supplemented with the following: dinoseb (50 mg/L), glucose or fructose (500 mg/L), $NH_4Cl$ (1.0 g/L), $MnCl_2.4H_2O$ (0.5 mg/L), $H_3BO_3$ (0.05 mg/L), $ZnCl_2$ (0.05 mg/L), $CuCl_2$ (0.03 mg/L), $Na_2MoO_4.2H_2O$ (0.01 mg/L), $CoCl_2.6H_2O$ (0.5 mg/L), $NiCl_2.6H_2O$ (0.05 mg/L), $Na_2SeO_3$ (0.05 mg/L), and a vitamin solution recommended by Wolin et al., *J. Biol. Chem.* 238:2882–2886 (1963). Yeast extract was added to the culture solution to a concentration of 0.5 g/L. Yeast extract served as a convenient source of additional carbon and energy for the microorganisms, as well as a source of additional vitamins and cofactors.

For culturing under denitrifying (anaerobic) conditions, the aerobic culture medium was supplemented with 1 g/L $KNO_3$, boiled under nitrogen gas, and sealed in glass containers with butyl rubber stoppers before inoculation. Culturing under denitrifying conditions is a way of selecting for facultative anaerobes. Under such conditions, nitrate is employed by the respiring microbes as an electron acceptor rather than oxygen as used by respiring aerobic microorganisms. Facultative anaerobes can be cultured in either aerobic or anaerobic environments.

A reduced anaerobic mineral medium (RAMM) was used for culturing the microorganisms under anaerobic conditions. RAMM comprised the same ingredients as listed above for aerobic cultures, but with 10 mg/L resazurin added as a redox indicator, 10 mg/L $NaS_2O_4.2H_2O$ added as a reducing agent, and 1.2 g/L $NaHCO_3$. (Preferably, 0.1 g/L yeast extract is also added.) Anaerobic cultures were grown in serum bottles and balch tubes sealed with butyl rubber stoppers, using strict anaerobic procedures, as detailed in Ljungdahl and Wiegel, "Working with Anaerobic Bacteria," in Demain and Solomon (eds.), *Manual of Industrial Microbiology and Biotechnology*, American Society for Microbiology, Washington, D.C. (1986) pp. 84–96.

Several isolates of microorganisms which could aerobically transform dinoseb were obtained from the supernatant liquid of the chemostat containing glucose, dinoseb, and $NH_4Cl$. Characteristics of these isolates are presented in Table 1.

TABLE 1

| | | | | | | | | |
|---|---|---|---|---|---|---|---|---|
| | | | | Isolates That Aerobically Transform Dinoseb | | | | |
| | Gram | Colony[a] | | Dinoseb Transformation When: | | | | |
| Isolate | Reaction | Shape | Morphol. | Oxidase | Catalase | Facultative | microaerophilic | denitrifying |
| TDN-1 | + | rods | R, O, P | + | + | no | yes | no |
| TDN-2 | − | rods | I, T | +/− | + | yes | yes | yes |
| TDN-3 | − | rods | R, T | − | + | yes | yes[b] | no[b] |
| TDN-4 | +/− | rods | R, Y | + | + | yes | yes | no |
| TDN-5 | +/− | cocci | S, T | +/− | + | yes | yes | yes |

[a]Colonial Morphologies: R = round, I = irregular, S = spreading, T = transparent, O = opaque, Y = yellow, P = produces yellow-green pigment.
[b]Dinoseb transformation in this strain is inhibited by nitrate Under microaerophilic conditions, every strain caused the dinoseb-containing culture medium to turn bright red. Such transformation was not noted with any of the strains in aerated dinoseb-containing cultures. As used herein, the term "microaerophilic conditions" refers to a culture environment having an appreciably depressed concentration of dissolved oxygen as compared to aerobic conditions, but not so low as to be strictly anaerobic. Under such conditions, aminoaromatics can still undergo polymerization reactions. This is in contrast to strictly anaerobic conditions under which such polymerization reactions are blocked. Microorganisms termed "microaerophiles" undergo optimal growth under microaerophilic conditions.

The red substance obtained under microaerophilic conditions with all the strains could not be extracted with organic solvents, nor could it be resolved by thin-layer chromatography (TLC). Analysis confirmed that the red substance was the amino derivative of dinoseb. After two to three weeks, the red color faded and a brown precipitate formed. TLC analysis of the brown precipitate showed a continuous smear with no discernable bands. These results indicate that dinoseb is transformed under microaerophilic conditions to an amino form which is oxidatively polymerized to larger random-length molecules and not degraded.

Strains TDN-2 and TDN-5 appeared to be facultative anaerobes and were able to carry out the transformation of dinoseb to the red metabolite under denitrifying (anaerobic) conditions, in which case the brown precipitate did not form.

To quantify the transformation of dinoseb by the strains of Table 1, dinoseb concentrations were determined by High Performance Liquid Chromatography (HPLC) using a binary gradient of 10% tetrahydrofuran and methanol (solution A) and 1% acetic acid and water (solution B) on a 250×2 mm Phenomenex "Spherex" 5 $\mu$m C18 reverse-phase column (Phenomenex Corp., Rancho Palos Verdes, Calif.). A Hewlett-Packard Model 1090A instrument, equipped with a diode-array detector and a computerized data system, was used for the analyses. The solvent flow rate was 0.4 mL/min, and the column temperature was 40 C. The gradient program was a ten-minute gradient from 60% solution A plus 40% solution B to 100% solution A, followed by five minutes at 100% solution A. Detection of dinoseb and transformation products thereof was by use of the diode-array detector, measuring UV absorption at 268, 225, and 385 nm, with continuous scanning of the absorption spectrum from 190 to 450 nm.

HPLC analysis of the culture medium from strains TDN-2 and TDN-5, of Table 1 also showed accumulation of a single dinoseb-transformation product with a HPLC retention time of 2.05 minutes. Dinoseb transformation by strain TDN-3 was inhibited by nitrate in both microaerophilic and denitrifying conditions. No dinoseb transformation occurred in anaerobic cultures of TDN-4, but transformation did occur when the flasks were opened and the cultures exposed to air. Strain TDN-1 was obligately aerobic and only transformed dinoseb under microaerophilic conditions.

As indicated in Table 1, these isolates of dinoseb-transforming microorganisms were taxonomically diverse, although no definite species identifications were made. Despite this apparent species diversity, the isolates appeared to carry out similar reactions when transforming dinoseb.

The above results indicate that, in oxygen-containing environments, the isolates obtained from the aerobic supernatant of the chemostat only reduced the nitro groups of dinoseb, thereby forming amino products that were subsequently oxidized by extracellular enzymes to form amorphous polymeric compounds, as diagrammed in FIG. 1.

Since the dinoseb is apparently not actually degraded via such an aerobic process, but merely "transformed" into an amorphous polymer, the products of the process probably latently retain all the toxicity of dinoseb. Thus, it appears that aerobic bacteria such as certain of the strains listed in Table 1 do not actually detoxify dinoseb and would, therefore, not be appropriate for use in bioremediation of nitroaromatic contaminants in wastewaters or contaminated soils.

Although the above results were useful in elucidating the mechanism of dinoseb transformation in aerobic environments, it became clear that a biological method for degrading dinoseb and related microaromatic compounds from contaminated soils and waters must include the use of microorganisms selected in a dinoseb-containing anaerobic environment. As a result, microorganisms resident in the anaerobic sediment of the chemostat supplied with medium containing 100 ppm dinoseb plus 0.5 g/L glucose and 1 g/L $NH_4Cl$ were cultured and tested.

A consortium (stable mixed population) of anaerobic microorganisms capable of degrading dinoseb to non-aromatic products was enriched from the population of such organisms in the chemostat as follows. Sediment from the chemostat consisting of soil was used to inoculate strictly anaerobic medium comprised of the mineral nutrient solution described above with added 1 g/L fructose, 1 g/L $NH_4Cl$, and 100 ppm dinoseb. After five weeks' incubation, the bright yellow color of the medium (due to the presence of dinoseb) changed to a bright orange, then faded to colorlessness followed by development of turbidity. This activity could be maintained in mineral medium for three or four sediment-free transfers, but not in medium containing 0.2 g/L yeast extract or 5% rumen fluid. Sediment-free anaerobic dinoseb-degrading cultures could be maintained indefinitely by making three transfers in mineral medium, followed by one transfer in yeast extract-containing medium, followed by further mineral medium transfers. After eighteen months of such transfers, the dinoseb-degrading cultures remained stable in the yeast-extract containing medium, which resulted in 5-to 10-fold faster degradation of dinoseb than in mineral medium without yeast extract.

Degradation of dinoseb to non-aromatic products by the anaerobic consortium did not occur unless strict anaerobic procedures were followed during preparation of the media and during culture transfers. This indicates that actual dinoseb degradation to non-aromatic products, as opposed to mere transformation, is an anaerobic process.

Several parameters should be controlled for optimal dinoseb degradation by the anaerobic consortium. These include temperature, nitrogen and pH.

Figure 2:
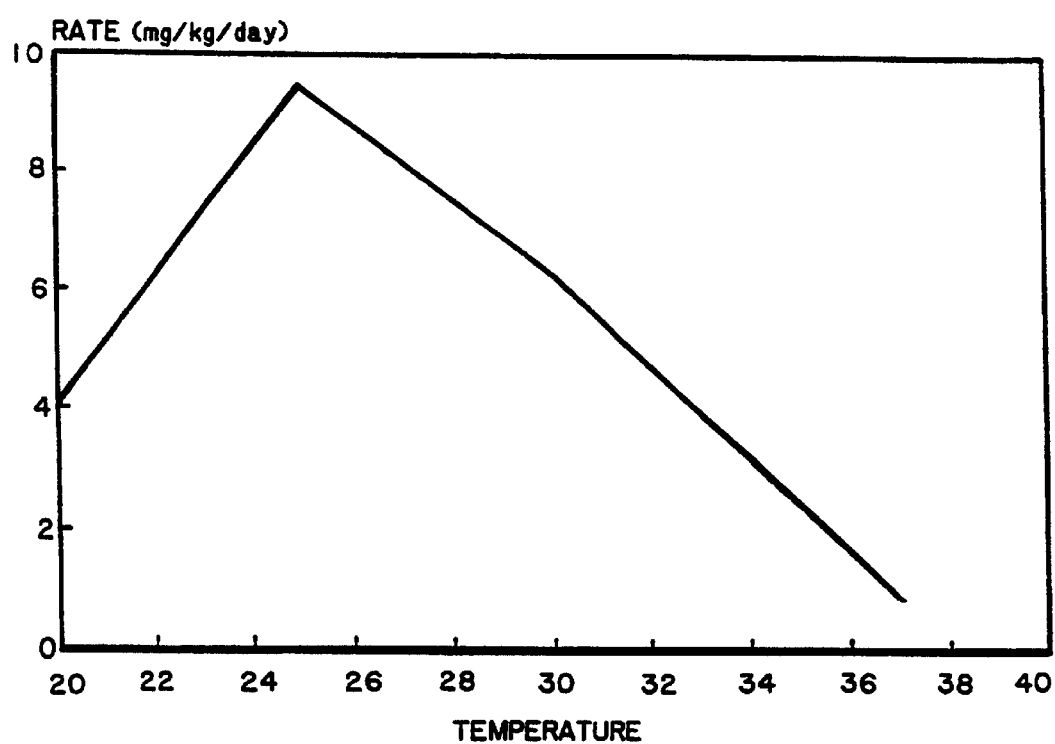
FIG. 2 is a graph showing the rate of biodegradation of dinoseb according to the present invention as a function of temperature.

As shown in FIG. 2, the optimal temperature for dinoseb degradation is about 25 C. Although FIG. 2 only covers a range from 20° C. to 40° C., a useful temperature range would be within the range for mesophilic microorganisms, generally between 10° C. and 40° C. Temperatures higher than about 40° C. would either kill important microorganisms or shut down key enzymatic reactions. Lower temperatures within this range, including temperatures within the range 10° C. to 20° C., would merely result in a slower metabolic rate of the microorganisms, the rate generally dropping by about half for every ten-degree drop in temperature.

Figure 3:
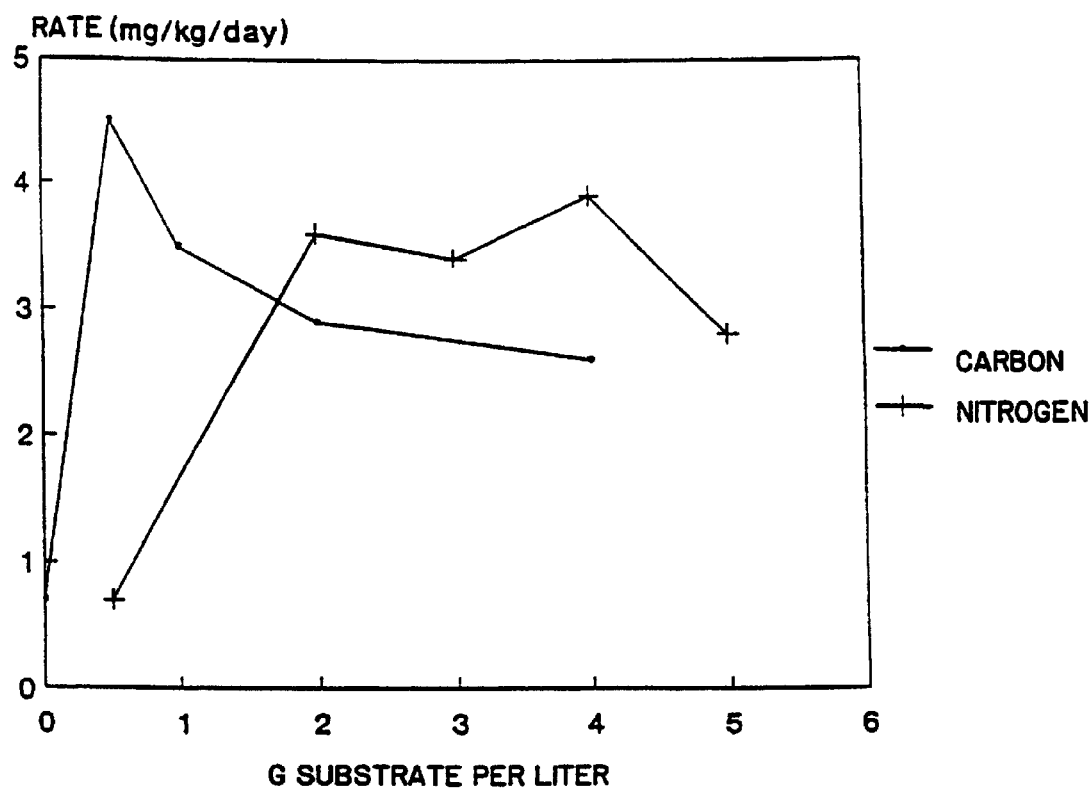
FIG. 3 is a graph showing the relationship to dinoseb biodegradation rate of various concentrations of sugar (carbon), and ammonium chloride (nitrogen) for the anaerobic consortium of microorganisms.

As shown in FIG. 3, the optimal sugar concentration (either fructose, glucose, or other simple sugar is suitable) is about 0.5 g/L, as indicated by the "carbon" line. The optimal $NH_4Cl$ concentration is about 4 g/L, as indicted by the "nitrogen" line. However, the anaerobic culture is largely insensitive to $NH_4Cl$ concentration between about 1 and 5 g/L. $NH_4Cl$ serves as an important source of nitrogen for the anaerobic microorganisms. Other nitrogen-containing compounds can also be used, so long as the nitrogen is in a form such as ammonium ion or amino groups. The nitrogen source cannot be a nitrate because nitrates inhibit the process of nitroaromatic degradation by these microorganisms.

Figure 4:
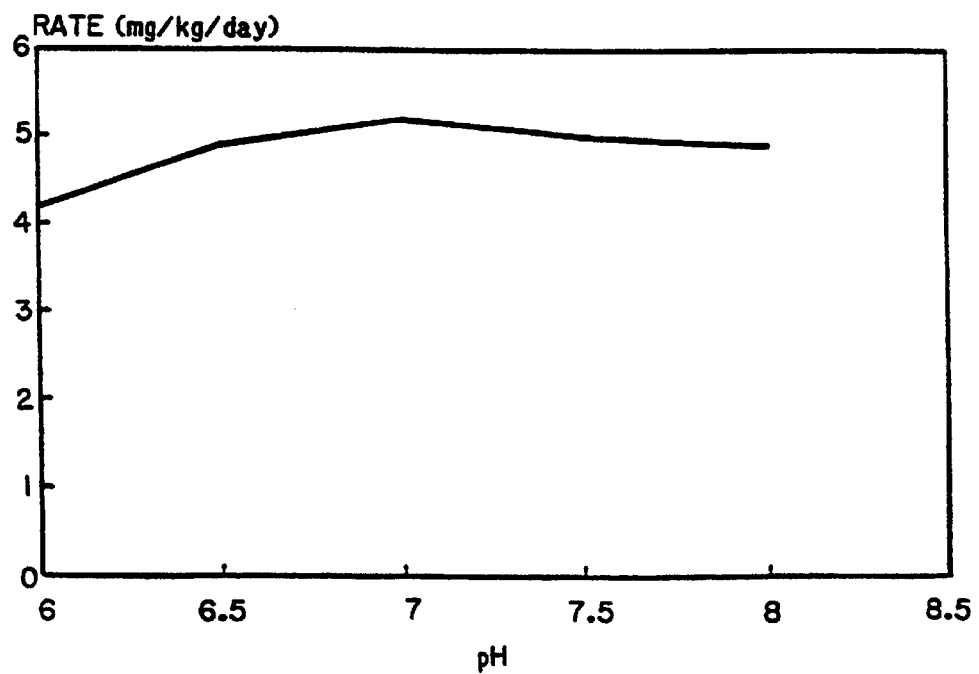
FIG. 4 is a graph showing the rate of biodegradation of dinoseb according to the present invention as a function of pH.

Finally, the optimal pH is about 7, as shown in FIG. 4, but the anaerobic culture appears to be largely insensitive to pH values between 6 and 8.

Figure 5:
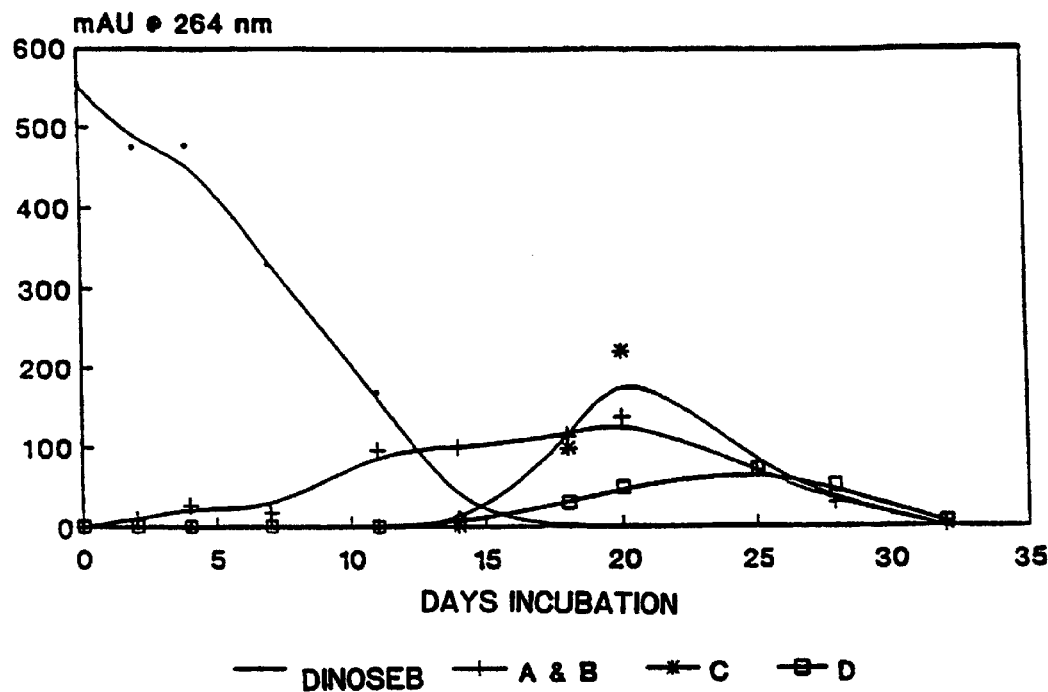
FIG. 5 is a graph showing the kinetics of anaerobic biodegradation of dinoseb by the anaerobic consortium to intermediary compounds and the subsequent disappearance of the intermediary compounds.

The anaerobic consortium degraded dinoseb via a series of intermediate aromatic products (A, B, C, and D, as shown in FIG. 5) which could be detected by HPLC. As determined by UV absorption spectra, no further aromatic products could be detected after thirty days, indicating that complete cleavage of the aromatic ring occurred. Such aromatic cleavage is a key step in the degradation of dinoseb to non-toxic compounds.

The stable consortium of anaerobic microorganisms contained at least three bacterial morphologies, including: short coccobacilli, 1–1.5 $\mu$m long; medium-sized rods, 0.75×2 $\mu$m; and large rods, 1–1.5×4 $\mu$m. Briefly exposing the consortium to air before anaerobic incubation resulted in elimination of the large rods. Also, dinoseb degradation did not proceed beyond intermediate D (FIG. 5). When the anaerobic consortium was used to inoculate dinoseb-containing aerobic media, a single bacterial species grew. That species was a gram-negative rod which grew as a coccobacillus under anaerobic conditions. The coccobacillus transformed dinoseb to a single uncharacterized product in aerobic cultures and to a different product in anaerobic cultures. The bacterium also was catalase positive, oxidase negative, and most closely matched *Klebsiella oxytoca* (similarity index 0.677), using the BioLog GN identification system (Hayward, Calif.). The BioLog GN identification system is a method of testing bacteria for utilization of ninety-five different carbon substrates, where the resulting pattern growth is compared with a database of patterns for known species of bacteria.

Figure 6:
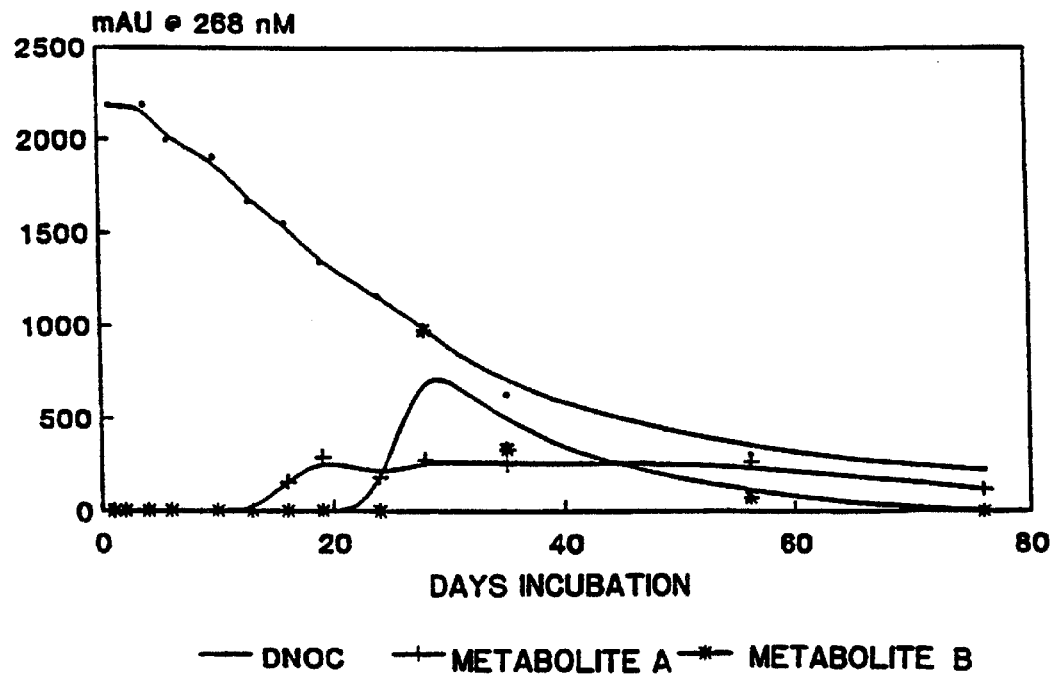
FIG. 6 is a graph similar to FIG. 5 showing the kinetics of anaerobic biodegradation of 4,6-dinitro-o-cresol by an anaerobic consortium previously acclimated to dinoseb.
Figure 7:
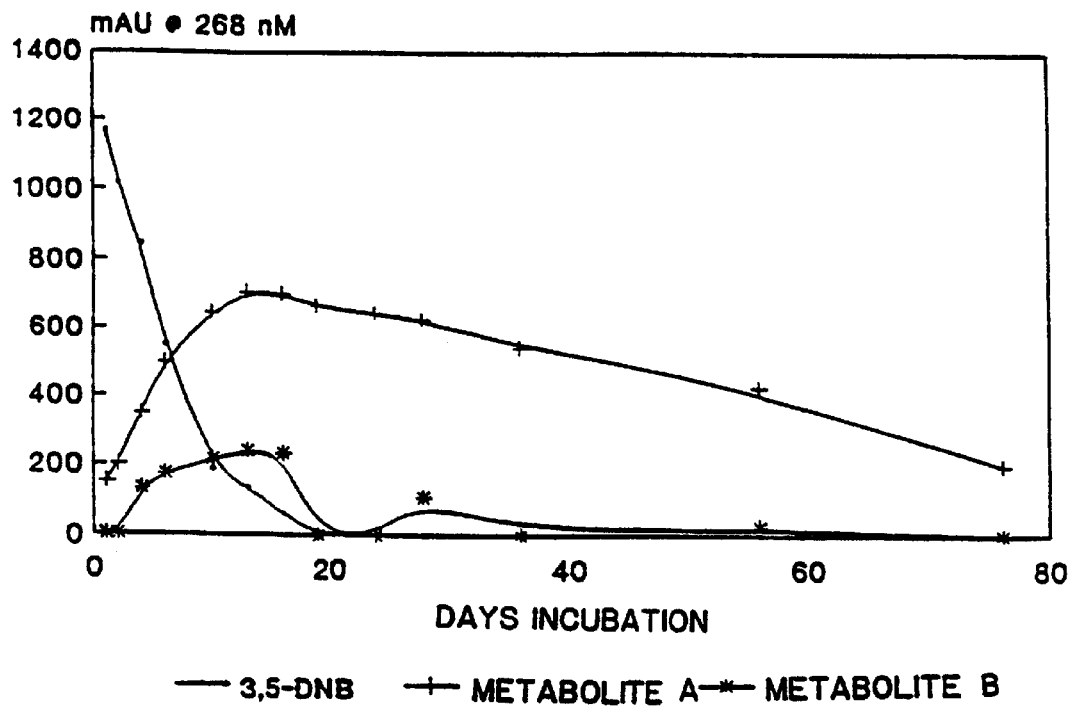
FIG. 7 is a graph similar to FIG. 5 showing the kinetics of anaerobic biodegradation of 3,5-dinitrobenzoate by an anaerobic consortium previously acclimated to dinoseb.
Figure 8:
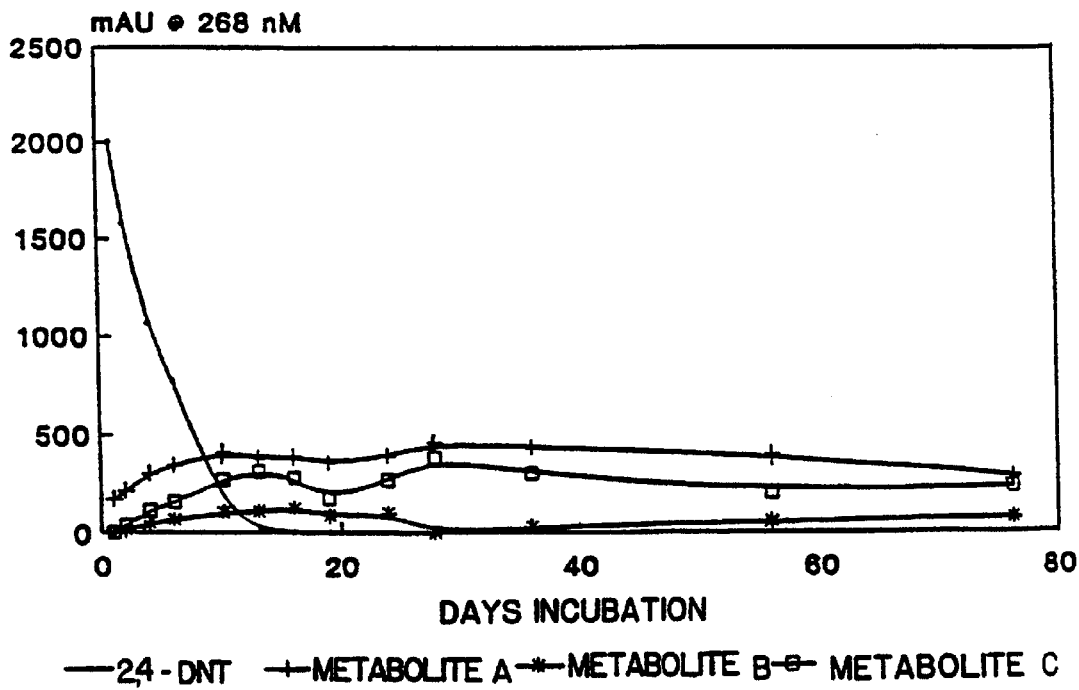
FIG. 8 is a graph similar to FIG. 5 showing the kinetics of anaerobic biodegradation of 2,4-dinitrotoluene by an anaerobic consortium previously acclimated to dinoseb.
Figure 9:
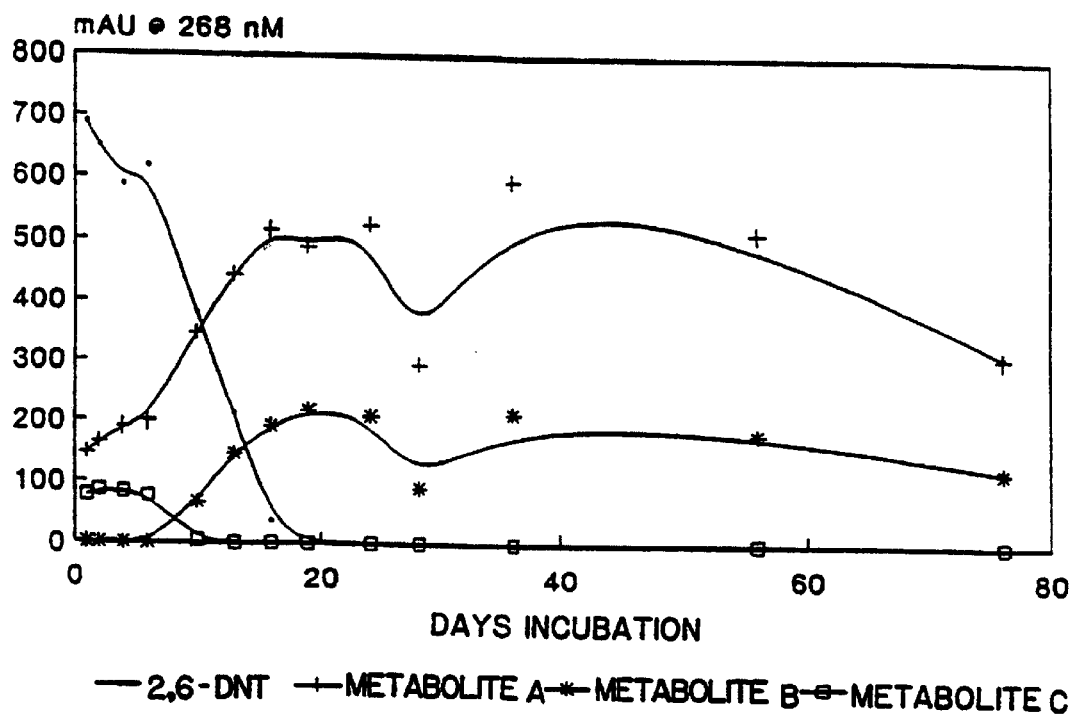
FIG. 9 is a graph similar to FIG. 5 showing the kinetics of anaerobic biodegradation of 2,6-dinitrotoluene by an anaerobic consortium previously acclimated to dinoseb.
Figure 10:
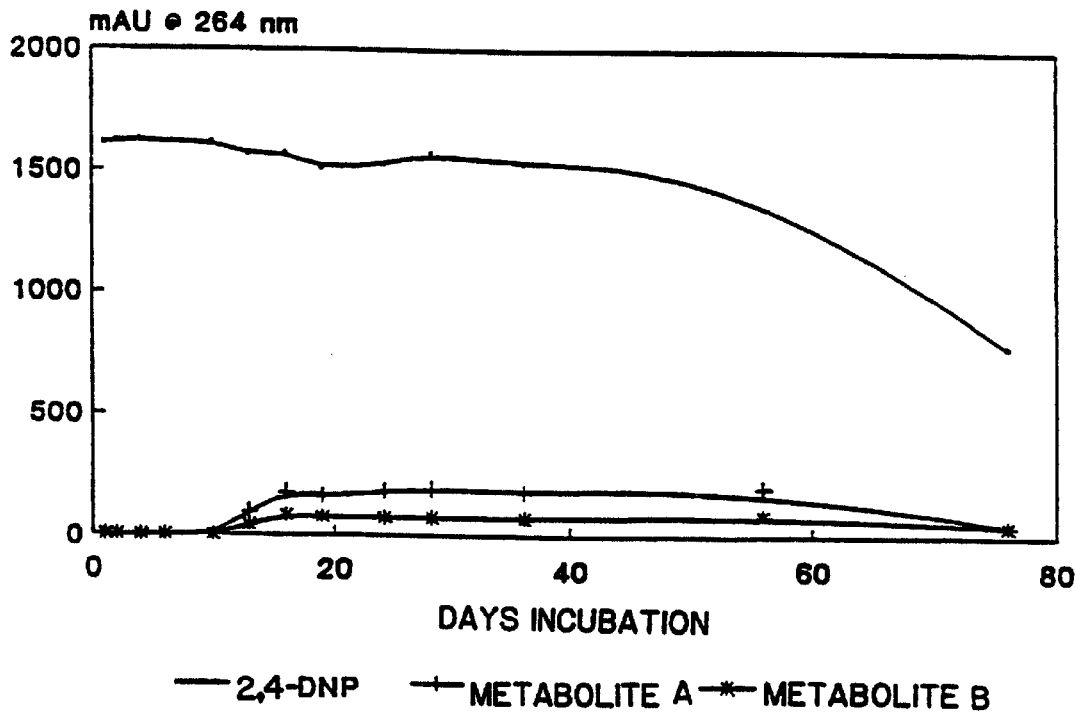
FIG. 10 is a graph similar to FIG. 5 showing the kinetics of anaerobic biodegradation of dinitrophenol by an anaerobic consortium previously acclimated to dinoseb.

The anaerobic consortium was tested for its ability to degrade other nitroaromatic compounds. Utilization of other nitroaromatic substrates was determined by growing cultures in medium similar to that described above, but with 50 ppm of the appropriate nitroaromatic compound substituted for dinoseb. The anaerobic consortium was able to completely degrade 4,6-dinitro-o-cresol (DNOC, FIG. 6) and 3,5-dinitrobenzoate (3,5-DNB, FIG. 7) to non-aromatic compounds. 2,4-dinitrotoluene (2,4-DNT, FIG. 8) and 2,6-dinitrotoluene (2,6-DNT, FIG. 9) were degraded to intermediate products, but it was unclear whether or not the products were eventually degraded to non-aromatics. After sixty days, the concentration of 2,4-dinitrophenol (2,4-DNP, FIG. 10) began to decline, but the parent compound persisted for at least four months in these cultures. Degradation of these other nitroaromatic compounds was much slower than for dinoseb.

Figure 11:
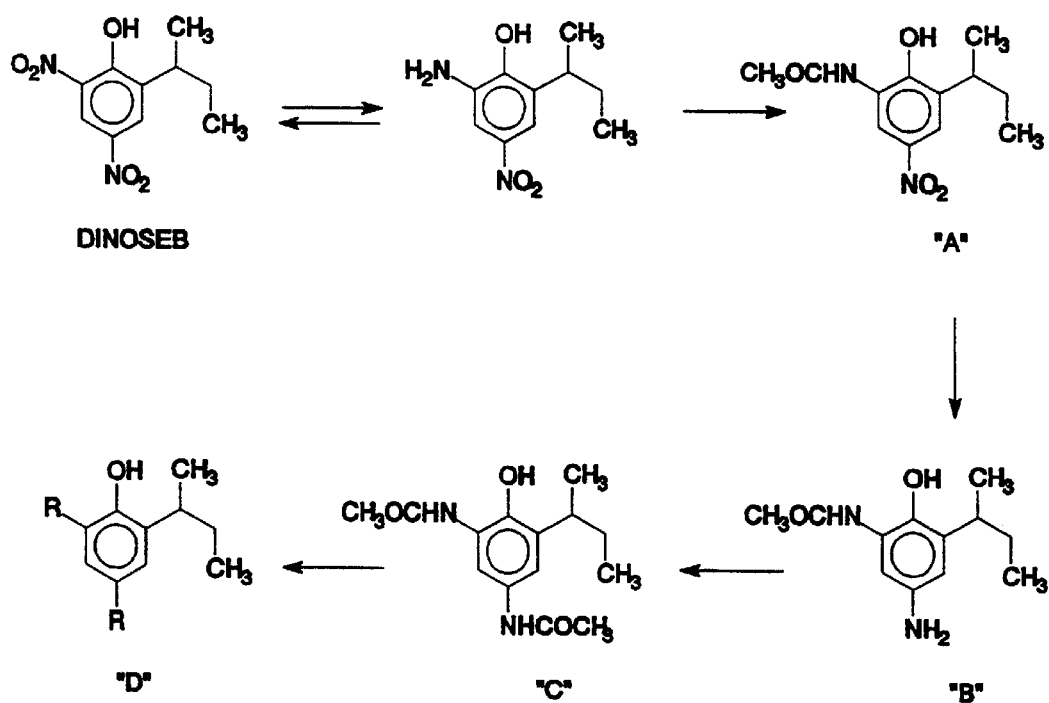
FIG. 11 is a schematic depiction of a reaction pathway for the anaerobic biodegradation of dinoseb according to the process of the present invention.

A dinoseb anaerobic degradation pathway consistent with the above results is shown in FIG. 11.

Figure 12:
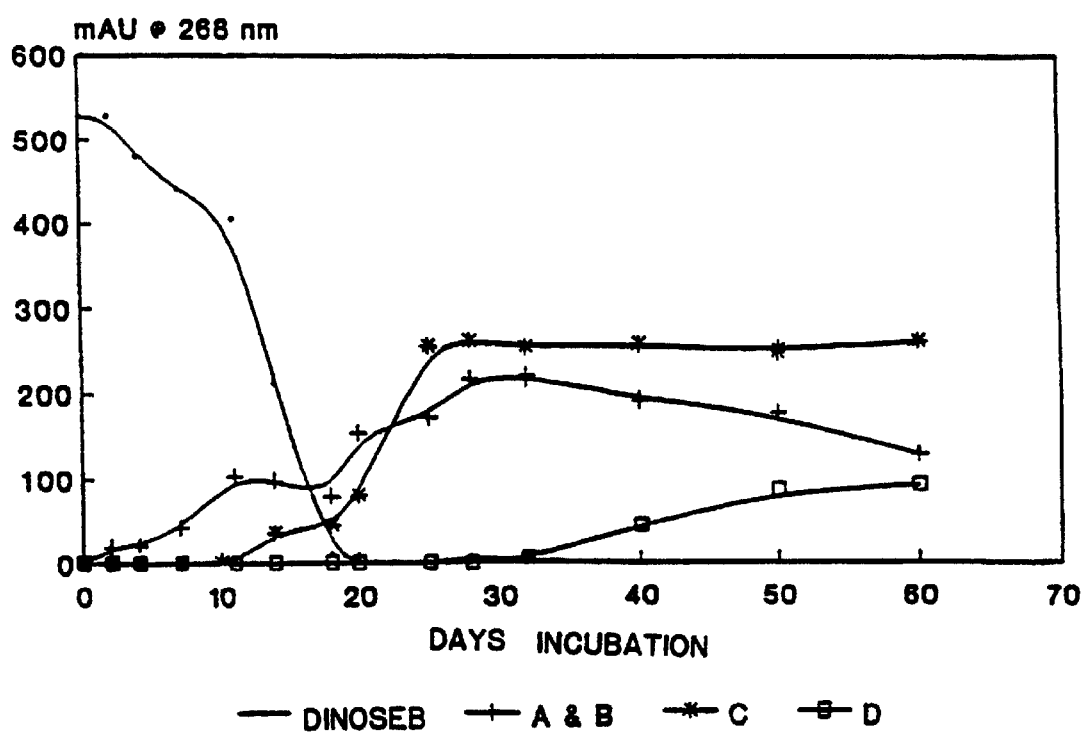
FIG. 12 is a graph showing the effect of BESA, an inhibitor of methanogenesis, on the anaerobic biodegradation of dinoseb by an anaerobic consortium.

When bromoethanesulfonic acid (BESA), a specific inhibitor of methanogenesis, was added to the anaerobic consortium at 200 $\mu$M concentration, dinoseb degradation was slowed and products C and D accumulated (FIG. 12). These products remained in the culture medium for at least another three months. Accumulation of C indicated that D is formed from C and that BESA at least partially blocked formation of D. Therefore, the reaction from C to D is probably a hydrogen-generating reaction. Since the reaction results in an increase in hydrophobicity, it probably involves removal of one or both acetamide groups.

The anaerobic dinoseb-degradation intermediates were tentatively identified as follows. Anaerobic dinoseb cultures were extracted and subjected to TLC, as described above, during both the early stages (orange color) and later stages (colorless) of dinoseb degradation. Extracts from the early stages yielded two TLC bands which were not present in uninoculated controls. GCMS analysis indicated that both bands contained multiple compounds. Similar analysis of the extract from the later stages of degradation yielded one band not present in uninoculated controls. The mass spectra showed fragmentation patterns similar to that for dinoseb, confirming that they correspond to dinoseb derivatives. The intermediates as identified are shown in FIG. 11.

The molecular formulas of the intermediates, based on isotope abundance calculations from the molecular weights (+/−0.005 AMU), are shown in Table 2. The intermediate with molecular weight 220 could not be assigned a molecular formula; however, the stated mass was expected from 2-sec-butyl-4-nitro-6-aminophenol. The major product in the later stages of degradation was identified as 2-aminobenzoic acid (anthranilic acid) by GCMS comparison with authentic standards.

TABLE 2

Accurate Mass Determinations and Molecular Formulas for Compounds Detected by GC/MS

| source | molecular mass | standard deviation | molecular formula | deviation from observed mass |
|---|---|---|---|---|
| dinoseb | 240.0699 | .0084 | $C_{10}H_{12}N_2O_5$ | .0047 |
| band 1 | 210.0891 | .0063 | NR | |
| band 1 | 220.0998 | .0081 | NR | |
| band 1 | 264.0995 | .0065 | NR | |
| band 2 | 234.0966 | .0071 | $C_{12}H_{14}N_2O_3$ | .0038 |
| band 2 | 165.1147 | .0046 | $C_{10}H_{15}NO$ | .0007 |
| band 1B | 136.060 | .0088 | $C_7H_8N_2O$ | .0035 |
| band 1B | 137.0508 | .0047 | $C_7H_7NO_2$ | |

NR = no reasonable formula could be calculated from this mass reading

Under anaerobic conditions the reduced dinoseb derivatives would not be subject to the oxidative coupling reactions found in the aerobic environment. Partially degraded molecules persisting as dissolved monomers are, therefore, available for further biodegradation by various anaerobic bacteria.

It is unclear why an external carbon source is required for dinoseb mineralization by the anaerobic consortium of microorganisms. One or more of these microorganisms may effect certain chemical changes to the dinoseb molecule, but derive no metabolic energy from such reactions or from the products of such reactions. Alternatively, microorganisms that carry out later steps in the degradation process might be inhibited by dinoseb. In the latter case, ring cleavage products would not be available for use by bacteria carrying out early steps in the degradation process.

Figure 13:
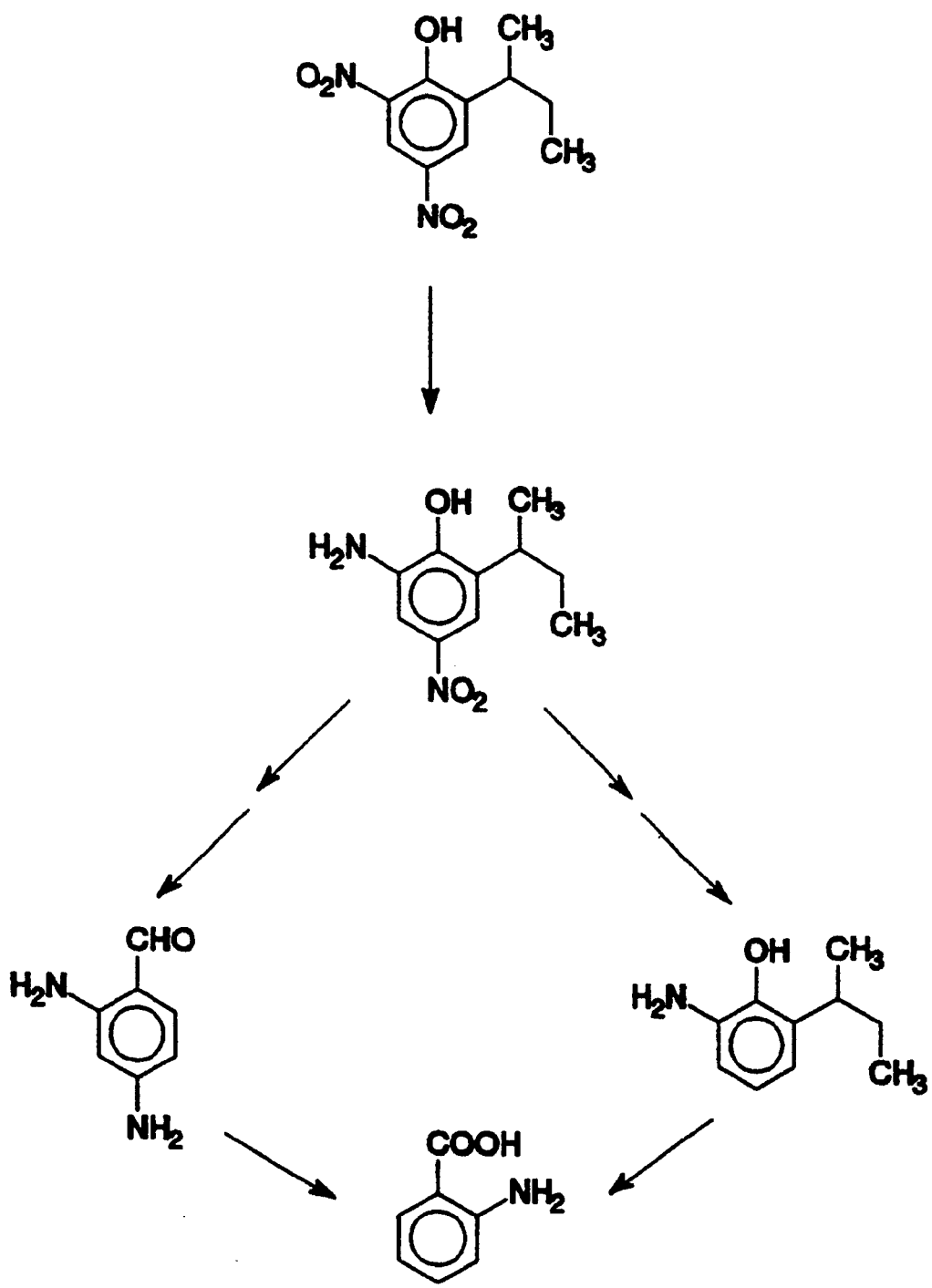
FIG. 13 is another schematic depiction of a reaction pathway for the anaerobic biodegradation of dinoseb according to the process of the present invention.

The results described above indicate, therefore, that dinoseb is biodegradable by the anaerobic consortium of microorganisms. The initial step involving reduction of nitro groups to amino groups appears to occur in a manner similar to that for rumen microorganisms. Intermediates detected having molecular weights of 220, 234, and 264 were not identified, but probably represent N-alkylated forms of reduced dinoseb. The alkyl side chain of dinoseb is also anaerobically removed, as indicated by formation of anthranilic acid. FIG. 13 shows a dinoseb degradation pathway consistent with the results above.

Studies in which [$^{14}$C]-ring-labeled dinoseb was degraded as above yielded [$^{14}$C]-acetate, indicating that dinoseb rings are cleaved. Additionally, we have found that the presence of nitroaromatics inhibits methanogenesis. However, the nitro groups are readily reduced to amino groups, after which methanogenesis resumes. The only intermediates identified to date are amino compounds, but numerous other "intermediates" have been found that remain to be specifically identified.

When tested with other nitroaromatic substrates, the anaerobic consortium was able to completely degrade nitrocresols or nitrobenzoates, but was unable to cleave the aromatic ring of nitrotoluenes or to degrade nitrophenols. It is probable that other selections performed in a manner similar to that described above would give rise to other anaerobic populations which can utilize these compounds. For example, passing a medium containing a nitrophenolic compound through a chemostat, as described above, inoculated with a diverse population of soil microorganisms would be expected to select for anaerobes capable of mineralizing nitrophenols. In other words, anaerobic consortia can be "tailored" for degrading a particular type of nitroaromatic compound.

Bioremediation of Fluid Media

As used herein, the term "fluid medium" refers to waters and slurries, including mud, comprising water plus soil or other particulate material.

The process of the present invention requires an aqueous fluid medium because anaerobiosis can only occur in aqueous environments. As a result, bioremediation of a contaminated dry soil requires that water be added, forming a mud slurry, to provide a sufficiently aqueous environment for metabolic activity by the anaerobic consortium of microorganisms. Such an aqueous environment is automatically provided when the process is to be applied to a contaminated wastewater.

In addition, the anaerobic consortium is unable to withstand prolonged exposure to oxygen. Consequently, an inoculum comprised of such microorganisms should not be added to a volume of soil slurry or wastewater to be subjected to biodegradation without first rendering the volume anaerobic. The transition to anaerobiosis should be as rapid as possible to preclude aerobic oxidative coupling of the contaminant nitroaromatics to polymeric forms via the action of indigenous aerobic microorganisms.

For the experiments described below, the anaerobic dinoseb-degrading consortium isolated as described above was maintained on a reduced anaerobic mineral medium (RAMM) consisting of: $KH_2PO_4$ (0.27 g/L), $K_2HPO_4$ (0.35 g/L), $NH_4Cl$ (1.5 g/L), glucose (0.5 g/L), yeast extract (0.1 g/L), $CaCl_2.2H_2O$ (15 mg/L), $MgCl_2.6H_2O$ (20 mg/L), $FeCl_2.2H_2O$ (4 mg/L), $MnCl_2.4H_2O$ (0.5 mg/L), $H_3BO_3$ (0.05 mg/L), $ZnCl_2$ (0.05 mg/L), $CaCl_2.2H_2O$ (0.05 mg/L), $NiCl_2.6H_2O$ (0.05 mg/L), $CuCl_2$ (0.03 mg/L), $NaMoO_4.2H_2O$ (0.01 mg/L), $NaHCO_3$ (2.4 g/L), and 1 ng/L resazurin. Cultures were incubated in darkness without shaking at 30° C. Strict anaerobic procedures were followed during all media preparations and transfer operations. Ljungdahl and Wiegel, "Working with Anaerobic Bacteria," in Demain and Solomon (eds.), *Manual of Industrial Microbiology and Biotechnology*, American Society for Microbiology, Washington, D.C. (1986).

In order to sustain anaerobiosis in the present process, a source of readily-metabolizable carbon, such as sugar, is required as a supplement. Preferably, the carbon source is a complex carbohydrate from which sugars are "released" over a period of time, rather than a supply of sugar that is completely "available" for immediate consumption. Because complex carbohydrates must be enzymatically cleaved to yield metabolizable sugar, they allow maintenance of strict anaerobic conditions in the fluid medium to be extended for a time period sufficient to biodegrade the particular concentration of contaminant nitroaromatic without the need to add more carbon source. For example, if a large amount of an "available" sugar, such as glucose or fructose, were added to an aerobic aqueous slurry of soil, anaerobiosis would be quickly achieved. However, maintenance of strict anaerobiosis for the several weeks that may be required to achieve complete degradation of the nitroaromatic would be difficult due to an initially very high rate of sugar metabolism followed by premature exhaustion of the sugar supply.

Although sugar could be added at one or more additional times during maintenance of anaerobic conditions before complete nitroaromatic degradation was achieved, the added sugar would have to be added in controlled amounts at specific times and mixed each time into the fluid being treated. Such adding and mixing impart unnecessary complexity to the method. Further, use of more complex carbohydrates, such as starch, as a carbon source results in a steadier degradation rate. Repeated additions of sugar result in an undulating rate which is less efficient.

In view of the above, desired characteristics of the carbon source include a high energy content, ready metabolizability, low numbers of indigenous heterotrophic bacteria which might compete with the anaerobic inoculum, and sustained metabolic availability sufficient to maintain prolonged steady rate of anaerobiosis. On the basis of these criteria, a hydrolyzable polysaccharide such as starch is a more suitable carbon source than free sugar.

After evaluation of a number of starchy by-products from various food processing plants, a preparation of dewatered solids from a potato processing plant was selected as the preferred carbon source. The characteristics of the potato waste included: 42% solids, 215 mg/g available starch, 6.7 mg/g total nitrogen, $2.6 \times 10^4$ culturable hetertrophic bacteria per gram, and $8 \times 10^3$ culturable amylolytic (able to hydrolyze starch) bacteria per gram. Chief advantages of starchy potato waste are available in large amounts and at a low cost. However, any vegetable or grain starch would probably suffice.

Candidate starchy carbohydrates were analyzed for solid content by weighing after oven drying, and for total nitrogen content by the Kjeldahl procedure commonly known in the art. Available starch was determined by incubating sterilized 1-gram samples with 300 units of α-amylase and 100 μL of diazyme L-100 (Miles Pharmaceuticals, Elkhart, Ind.) for twenty-four hours in 10 mL of sterile 0.4 M phosphate buffer, pH 7.0. After incubation, the samples were diluted to 100 mL and analyzed for reducing sugars using the dinitrosalycilate assay with similarly prepared glucose as a standard. Miller, *Anal. Chem.* 31:426–428 (1959). Available starch was assayed as mg sugar released per gram dry weight of starchy carbohydrate. Numbers and types of bacteria in starchy carbohydrates were determined by standard plate counts in aerobic mineral medium agar containing (for total heterotrophic counts) 2 g glucose, 0.4 g yeast extract, 1 g $NH_4Cl$, and 1 g $NaNO_3$ per liter, or (for amylolytic bacteria) 2 g soluble starch, 1 g $NH_4Cl$, and 1 g $NaNO_3$ per liter for amylolytic bacteria.

Since the anaerobic consortium cannot withstand prolonged exposure to air, it is necessary to pretreat the volume of wastewater or soil slurry with a rapid aerobic fermentation step to deplete oxygen in the volume and achieve anaerobiosis before adding the anaerobic consortium. The transition from aerobic fermentation to anaerobiosis should be as rapid as possible to preclude oxidative coupling of aminoaromatic derivatives of the contaminant nitroaromatic in the aerobic step. According to the results of tests performed using loamy sand and rich silt-loam soils, simply flooding the soil with water does not produce sufficiently rapid anaerobiosis. Mere addition of sugar produces rapid anaerobiosis by an initial high rate of aerobic fermentation that rapidly consumes the available oxygen in the liquid. However, as discussed above, use of sugar as a carbon source instead of a complex carbohydrate, such as starch, usually results in premature exhaustion of the carbon source. Also, even with elevated concentrations of added sugar, at least partially aerobic conditions often reform before completion of the nitroaromatic degradation. Use of dewatered potato solids or other starchy carbohydrate that is metabolized more slowly than free sugar results in a satisfactorily rapid anaerobiosis following aerobic fermentation, while yielding a sustained sugar concentration over the period of time required to completely degrade the contaminant nitroaromatic.

To evaluate the relative effectiveness of starchy carbohydrates as a carbon and energy source versus a sugar such as glucose alone, 300-g samples of various types of soil, such as loamy sand and rich silt-loam, were individually placed in 1-L Erlenmeyer flasks and flooded with 200 mL of 0.4 M phosphate buffer (pH 7) to form a mud slurry. Flasks were covered with aluminum foil and incubated without shaking at 25° C. At various times during incubation, both pH and redox potential of the slurry were measured potentiometrically at 0, 1, and 3 cm beneath the liquid surface. A 1 mL sample was also removed for each analysis of residual sugar. A redox potential of −200 mV or less was indicative of a strictly anaerobic condition in the liquid.

The amount of starchy carbohydrate to add to a volume of wastewater or mud slurry for particulate dosages of fermentative and anaerobic organisms may have to be determined experimentally and optimized for a particular soil or wastewater and the particular type and concentration of contaminant nitroaromatic. To reduce costs in the actual bioremediation process, the amount of starch should be determined that will just sustain anaerobic conditions for the time required to achieve the desired degree of nitroaromatic degradation and no longer.

Any of a number of species of fermentative amylolytic microorganisms indigenously present in the starchy carbohydrate can serve to hydrolytically cleave the starch into constituent sugars when the starch is added to a volume of wastewater or slurry of soil. Such fermentative microorganisms would include aerobic and/or facultative microorganisms. Starch cleavage occurs via amylase enzymes secreted by the microorganisms into the surrounding aqueous medium. Although amylase action is optimal in aerobic environments, the enzyme will continue to hydrolyze starch when the medium becomes anaerobic. Additionally, many facultative amylolytic microorganisms will survive and continue to secrete amylase after a medium has been converted from aerobic to anaerobic. If sugar is used as the carbon source, the fermentative microorganisms need not be amylolytic.

In a series of incubation tests where the soil contained 25 ppm dinoseb, anaerobiosis occurred only after several days in the presence of the starchy potato by-product, where the initial aerobic fermentation was performed by fermentative amylolytic bacteria (representing a number of species) indigenous to the starchy potato by-product. Several days to achieve anaerobiosis is too long. Evidently, the indigenous bacterial population was adversely stressed by the dinoseb and unable to metabolically respond in a rapid manner. To selectively enrich for dinoseb-resistant amylolytic bacteria, additional starchy potato by-product and dinoseb (to 100 ppm) were added to a flask from these experiments. After a prolonged incubation to achieve selection, several dinoseb-resistant bacteria were isolated from the flask. One strain (strain DSA1), identified as facultative *Klebsiella oxytoca* by the BioLog GN system, retained good amylolytic activity in the presence of 100 ppm dinoseb.

When dinoseb-containing soil received an inoculum of *Klebsiella oxytoca* strain DSA-1, along with the starchy potato by-product, a greatly reduced time to achieve anaerobiosis was noted. In the latter case, anaerobiosis was established almost as fast as in control soils lacking dinoseb. *Klebsiella oxytoca* strain DSA-1 was thus regarded as a preferred inoculation strain with which to achieve anaerobiosis for degrading dinoseb in the presence of a starchy carbohydrate.

Although *Klebsiella oxytoca* strain DSA-1 was the particular bacterium selected for in the above-described experiments involving dinoseb, it is expected that other selections performed in a similar manner using a source of starch containing indigenous aerobic and/or facultative "fermentative" microorganisms will probably yield other species and strains after selection. Additionally, it is expected that using a nitroaromatic other than dinoseb for supplying the selection pressure would probably give rise to other satisfactory fermentative species and/or strains resistant to the particular nitroaromatic. The lesson from these studies is that the indigenous microflora associated with starches are probably not sufficiently tolerant to most nitroaromatics to facilitate the required high initial rate of fermentation to achieve rapid anaerobiosis in a volume of soil slurry or wastewater containing nitroaromatic compounds. As a result, it will probably be necessary to employ an aerobic or facultative species and strain preselected against the particular nitroaromatics to be biodegraded.

In order to achieve anaerobiosis in the shortest amount of time, it is preferable to inoculate using a large dose of preselected fermentative microorganisms. Our studies indicate that a dose of about $10^7$ to $10^8$ CFU per gram dry soil or mL water is an effective dose. Cost constraints generally preclude larger doses. Also, larger doses generally do not achieve proportionately shorter times to anaerobiosis.

In another series of tests, bioremediations of 1-kg samples of each type of dinoseb-contaminated soil (loamy sand and silt-loam) were individually performed by adding water, starchy potato by-product, and pretreating the resulting slurry with a large inoculum (as above) of *Klebsiella oxytoca* strain DSA-1. After each slurry was rendered anaerobic (redox potential<−200 mV), it was inoculated with a similarly large dose of the dinoseb-degrading consortium of anaerobic microorganisms. Dinoseb was found to be completely converted to intermediate compounds within one week of anaerobic inoculation. After four weeks, the concentrations of the intermediate compounds declined below detectable limits. At the end of the four-week period, only 0.5 ppm of dinoseb could be Sohxlet-extracted from the treated loamy sand soil, and none could be extracted from the treated silt loam. By contrast, in the uninoculated loamy sand control, dinoseb did not decline. In the uninoculated silt loam control, dinoseb did decline after several days' lag time, but no intermediate compounds metabolically derived from dinoseb were detected.

In similar experiments, soils contaminated with like concentrations of 4,6-dinitro-o-cresol and 3,5-dinitrobenzoate were bioremediated within thirty days.

To perform the above experiments, soils were adjusted to 100 ppm dinoseb before adding any microorganisms or starchy carbohydrate by adding to the soil a solution of dinoseb in methanol and allowing the soil to dry completely afterward. For each soil sample, 1 kg dinoseb-supplemented soil was mixed with 2 g of the starchy carbohydrate. The mixture was inoculated with the amylolytic bacteria, placed in an open two-liter capacity erlenmeyer flask, and a sufficient volume 0.4 M phosphate buffer (pH 7) was added to saturate the water-holding capacity of the soil. When the redox potential of the soil solution became less than −200 mV, a 50 mL volume (O.D. ≈° 1) of the anaerobic consortium was injected below the surface of the soil. Samples (approximately 5 g each) were removed periodically, weighed and vortexed with 5 mL 0.1 N NaOH. Samples were centrifuged to remove the solids, and the supernatant was analyzed for dinoseb and its metabolites. At the end of the incubation, the remaining soil was extracted and analyzed for dinoseb.

Dinoseb concentrations were determined by high performance liquid chromatography (HPLC) using a binary gradient of 10% tetrahydrofuran in methanol (solution A) and 1% acetic acid in water (solution B) on a 250×2 mm Phenomenex "Spherex" 5 μm C18 reverse-phase column. Analyses were performed using a Hewlett-Packard Model 1090A instrument, as described above. Dinoseb was extracted from soils by Soxhlet extraction with ethyl acetate for five hours. Before extraction, each sample was amended with 200 μL of a 0.25% solution of 4,6-dinitro-o-cresol in methanol, which served as an extraction standard, and lyophilized. Samples were then amended with 100 μL of 0.01 M $H_2SO_4$. After extraction, the extracts were dried over anhydrous $NaSO_4$, evaporated under a vacuum, and dissolved in 5 mL of ethyl acetate. Parallel experiments utilizing [$^{14}$C]-dinoseb were performed to evaluate mass-balance relationships for dinoseb and its degradation products. Details are described below. Results are shown in Table 3.

TABLE 3

| | | Percent of Total Radioactivity | | | |
|---|---|---|---|---|---|
| Treatment | $CO_2$ | Polar Extract | Nonpolar Extract | Solid | Percent Recovery |
| Loamy Sand Inoculated | 29.6 | 43.3 | 5.11 | 4.0* | 82 |
| Loamy Sand Uninoculated | 0.3 | 0.8* | 100.8 | 6.7* | 108 |
| Silt Loam Inoculated | 32.1 | 29.9 | 3.5 | 8.9* | 74 |
| Silt Loam Uninoculated | 0.8 | 1.1* | 31.3 | 44.8 | 78 |

* = these values were not significantly different from background counts at the 90% confidence level.

Referring to Table 3, about 30% mineralization to [$^{14}$C]-$CO_2$ was obtained after thirty days' incubation of samples of inoculated soils, as compared to less than 1% for the uninoculated controls. Most of the remaining radioactivity in the inoculated soils was present as polar metabolites. Less than 10% of the radioactivity was associated with solids in the inoculated soils after extraction, as compared to nearly 45% in the silt-loam control. In the loamy sand control, virtually all of the radioactivity was associated with the nonpolar extract, which contained undegraded dinoseb. In addition, although methane was not quantified in these experiments, some radioactivity appears to end up as methane.

To perform the radiochemical studies described above, radiolabeled dinoseb (u-ring [$^{14}$C]-dinoseb) was synthesized from [$^{14}$C]-phenol and was 96% radiochemically pure, as determined by HPLC analysis and TLC coupled with liquid scintillation counting. After adding 1 μCi u-ring [$^{14}$C]-dinoseb to the soil, the flasks were stoppered and a glass trap containing 1 mL of 1 M KOH was suspended in each flask. The KOH solution was exchanged daily during incubations, rinsed with 1 mL water and counted with 18 mL of BioSafe II liquid scintillation cocktail (RPI Inc., Mt. Prospect, Ill.). At the end of the incubation, each soil culture was connected to a $CO_2$ trap consisting of a series of four stoppered serum bottles each containing 10 mL of 1 N KOH. The gaseous effluent first passed through a C18 "Sep-Pak" cartridge (Waters Associates, Milford, Mass.) wetted with methanol to remove volatile organics. Each soil culture was then acidified with 10 mL concentrated HCl, agitated, and flushed with nitrogen gas to drive off dissolved $CO_2$. One-mL samples from each trap were counted with 19 mL of BioSafe II.

Three 25-gram subsamples of each soil slurry were neutralized and extracted with 0.1 N NaOH. The extracts were neutralized, then passed through a "Sep-Pak" C18 cartridge which was rinsed with 1 mL water. The solid subsamples were dried, Soxhlet extracted, and the extracts were pooled with ethylacetate elutions from the "Sep-Pak" cartridges. From both the polar and non-polar extracts, 1 mL samples were counted with 19 mL of BioSafe II. Finally, 0.25 gm of each extracted soil sample was mixed with 19 mL BioSafe II and counted. All radioactive samples were counted in a Beckman Model 7000 liquid scintillation counter. A control flask for each soil type was treated similarly except that no bacterial inoculations were made.

In the above experiments, simply flooding the soils did not produce anaerobiosis in the resulting soil slurries, even in a slurry of the rich silt-loam soil. It is probable that anaerobiosis occurred within highly localized sites within the slurry, such as soil pores, but this was not sufficient to support growth of the oxygen-sensitive anaerobic consortium. In every case, exogenous carbon, preferably as a starchy carbohydrate metabolized by amylolytic microorganisms, was required to produce the requisite strict anaerobiosis that would allow growth of the subsequently added dinoseb-degrading anaerobic microorganisms.

The experiments described above show that exogenous, strictly anaerobic microorganisms can be used to degrade nitroaromatic chemicals in soil or wastewater. The mass balance and $^{14}$C data indicate that the anaerobic consortium mediated a complete destruction of dinoseb as a representative nitroaromatic, rather than mere polymerization of the compound, which occurred in the silt-loam soil in the absence of anaerobic inoculation.

The method of the present invention, therefore, comprises basically two stages: an initial fermentative stage wherein the wastewater or aqueous slurry of nitroaromatic-contaminated soil is fortified with a starchy carbohydrate and inoculated with "fermentative" (aerobic and/or facultative) amylolytic bacteria that hydrolyze the starch, metabolize a portion of the sugars produced by the hydrolysis, and consume the oxygen in the liquid; and a subsequent anaerobic stage wherein the wastewater or aqueous slurry of contaminated soil is inoculated with a consortium of anaerobic bacteria that metabolize the remaining sugar and degrade the contaminant nitroaromatic. This bioremediation method may be used for any soil or water contaminated with dinoseb or other nitroaromatic or aminoaromatic compounds subject to polymerization reactions in aerobic soil, such as 4,6-dinitro-o-cresol and 3,5-dinitrobenzoate.

Although anaerobiosis can be performed in an open environment, it is inefficient and difficult to control unless performed in a closed environment, particularly on a large scale. As a result, the method of the present invention is performed in the field, preferably in a suitably large liquid-containment vessel or the like.

Figure 14:
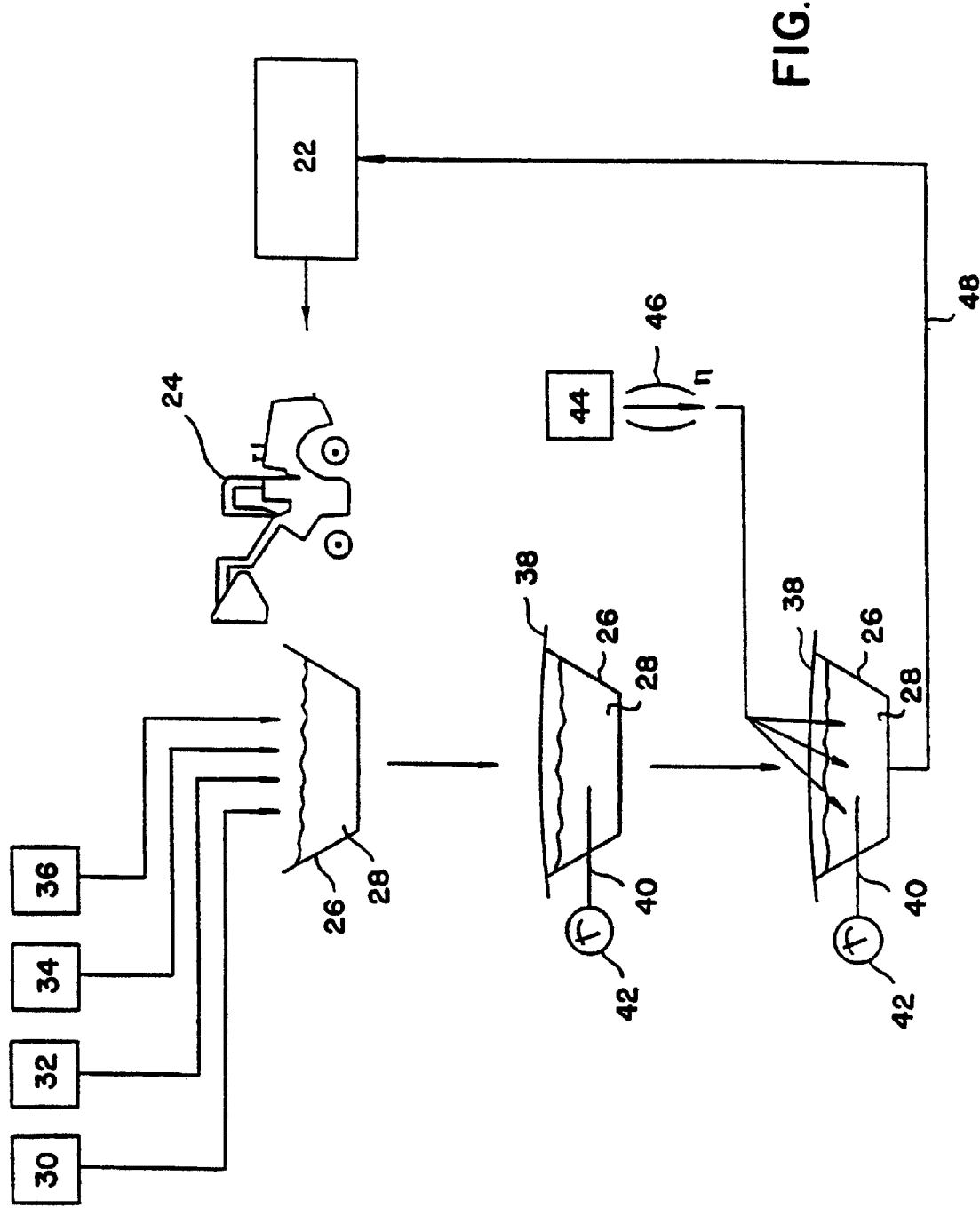
FIG. 14 is a representative schematic depiction of a process according to the present invention as it would be conducted at a field site.

FIG. 14 is a schematic representation of one embodiment of the process of the present invention, as it would be conducted in the field to bioremediate a nitroaromatic-contaminated soil. In FIG. 14, the contaminated soil 22 is transferred via equipment 24 to a plastic-lined pit 26 or the like. After the soil 22 is added to the pit 26, starchy carbohydrate 30, a nitrogen source 32, water 34, and an inoculum of fermentative amylolytic microorganism 36 are added to the soil 22, forming a slurry 28 in the pit 26. After forming the slurry 28, a cover 38 is placed over the pit 26, where the plastic-lined pit 26 and cover 38 together serve to exclude gaseous exchange between the slurry 28 and the atmosphere. The slurry 28 is monitored using a potentiometric probe 40 coupled to a readout 42 to enable one to determine when anaerobic conditions have developed in the slurry 28 (redox potential about −200 mV or less). After the slurry 28 reaches anaerobiosis, an inoculum of an anaerobic consortium 44 of microorganisms is added to the slurry 28 beneath the surface, after performing sufficient numbers of serial transfers 46 of the anaerobic microorganisms 44 to yield a suitably large dose. The slurry 28 is maintained in an anaerobic condition in the covered pit until the nitroaromatics are biodegraded, at which time the slurry 28 may be returned 48 to the original site.

The process of FIG. 14 is a batch process. In a batch process applied to nitroaromatic-contaminated wastewater (not shown), the contaminated water is simply conducted into the plastic-lined pit 26 of FIG. 14 or analogous vessel for bioremediation according to the present method. In the case of soil, it is usually necessary to add water to the soil to form a mud slurry, which is a more suitable environment for anaerobiosis than dry soil. Such a slurry will have a proportion of water relative to soil of about 15% to 20% (w/w) or more, depending upon the type of soil and the degree of nitroaromatic contamination, to preferably bring the soil at least to about 100% water-holding capacity. More water can be added, if desired. More water added to the soil lessens the effective concentration of the contaminant nitroaromatic.

Since most soils and many natural waters already have a broad spectrum of mineral nutrients available to support life, in many cases it will not be necessary to add to the water or mud slurry many of the supplementary mineral nutrients required for laboratory cultures. In virtually all cases, however, an extraneous nitrogen source 32 will be required, such as ammonium chloride. Many soils and most waters will also require extraneous phosphate (not shown), such as sodium or potassium phosphate. The nitrogen and phosphate requirements for the present process can be satisfied in many cases by merely adding ammonium phosphate (a common "fertilizer") as a supplement until the approximate desired concentration of ammonium and phosphate are attained. Since each soil and water is different, preliminary analysis of the soil or water may be needed to determine indigenous concentrations of ammonium and phosphate so that the proper amount of supplementary ammonium and phosphate can be determined so as to avoid waste.

As stated above, the nitrogen source 32 should not be nitrate because nitrates inhibit the ability of the anaerobic microorganisms to biodegrade nitroaromatics.

It may be necessary, particularly in the case of strongly acidic waters or soils contaminated with nitroaromatics, to adjust the pH of the fluid medium to within the preferred range of about 6 to 8. An inexpensive additive, such as lime, is satisfactory for elevating the pH. In most cases, however, significant pH adjustment will not be necessary. Extrapolating from the graph of FIG. 4, it would seem that pH values appreciably above or below (especially above) the preferred range of 6 to 8 would not cause a catastrophic depression of microbial metabolism required for bioremediation.

The preferred target concentrations of key nutrients (including contributions by the soil and/or water) are as given in the list of such ingredients in the nutrient solutions used in the studies described above. The ammonium concentration, as stated earlier, should preferably be between 0.4% and 0.5% (w/v), but a concentration between 0.1% and 0.6% (w/v) would suffice. The overall ionic strength of the water or slurry to be treated should preferably be approximately that of the laboratory cultures of microorganisms, but the microbes are tolerant to surprisingly large variations of ionic strength.

The temperature should preferably be between about 10°C. and 40°C., with the optimal temperature about 25°C. As discussed above, lower non-freezing temperatures tend to slow microbial metabolism and correspondingly increase the length of time required to achieve bioremediation.

While yeast extract is an important supplement for laboratory cultures, it is not necessary in virtually all field applications, since soils and wastewater often contain "vitamins," cofactors, and other products of natural organic processes utilizable by the microorganisms of the present process.

The inoculum of fermentative amylolytic microorganisms 36 should be added at a dose of $10^7$ to $10^8$ CFU (colony forming units) per gram dry soil or per mL water. Higher doses are usually not necessary. Lower doses may result in a longer-than-optimal time to reach anaerobiosis. In addition, an amount of starchy carbohydrate 30, determined as described above, is also added. Preferably, the amount of starchy carbohydrate added per unit amount of water or soil slurry is experimentally "tailored" to sustain anaerobiosis for a sufficient amount of time to achieve the desired degree of nitroaromatic degradation in the water or soil. Since types and concentrations of nitroaromatic contaminants will differ among various soils and waters, and since soils and waters themselves will differ, the optimal amount of starchy carbohydrate required will probably differ at each of various contaminated sites.

While the specific anaerobic consortium 44 of microorganisms described herein is suitable for degrading dinoseb and certain other nitroaromatics as described, other consortia of anaerobic microorganisms selected for and isolated in a manner as described herein, but using a nitroaromatic other than dinoseb may be more suitable for other nitroaromatics.

Although employing fermentative microorganisms to render the water or slurry anaerobic is the preferred method, other methods may be employed (not shown). However, it is anticipated that other methods may be prohibitively expensive. Such other methods include purging oxygen from the liquid using, for example, nitrogen or argon gas. However, gas-purging is typically slower and less efficient in achieving satisfactory anaerobic conditions than employing aerobic fermentation. Another method would require adding oxygen-scavenging agents (strong reducing agents) to the liquid. Although use of reducing agents may be efficient (and rapid), the disadvantage is that such agents represent other contaminants added to the water or slurry. As a result, use of microbial fermentation of sugar or starch is the preferred approach for achieving anaerobiosis.

After the contaminant nitroaromatic has been satisfactorily biodegraded in the volume of water or slurry contained in the covered pit 26 or vessel, the pit 26 or vessel may be drained and a new volume of contaminated water or mud slurry added for bioremediation. In a semicontinuous process, about 10% to 15% of the previous batch of treated water or slurry may be left in the pit 26 or vessel to aid in the inoculation of the subsequent batch. Additionally, such a semicontinuous process would preferably be controlled by various continuous electronic and chemical monitoring techniques known in the art, such as of dissolved oxygen and specific ions, as well as environmental conditions such as pH and temperature. Concentrations of nitroaromatic contaminants and their metabolic intermediaries can be discontinuously monitored using HPLC and gas chromatography, for example.

Having illustrated and described the principles of our invention with reference to detailed descriptions of process steps and specific examples, it should be apparent to those of ordinary skill in the art that the invention may be modified in arrangement and detail without departing from such principles. We claim as our invention all such modifications as come within the true spirit and scope of the following claims.

We claim:

1. A method for converting a nitroaromatic compound in a sample into a non-aromatic compound, comprising:
   providing a sample comprising a nitroaromatic compound;
   providing within the sample an anaerobic microorganism resistant to the nitroaromatic compound and capable of converting the nitroaromatic compound into a non-aromatic compound; and
   allowing the anaerobic microorganism to convert at least a portion of the nitroaromatic compound into a non-aromatic compound.

2. The method of claim 1 further comprising the step of adding a nutrient source comprising a carbohydrate to the sample.

3. The method of claim 2 where the nutrient source further comprises a member of the group consisting of a nitrogen source, a phosphorous source, and mixtures thereof.

4. The method of claim 2 further comprising providing within the sample a fermentative microorganism that is resistant to the nitroaromatic compound.

5. The method of claim 4 where the fermentative microorganism is selected from the group consisting of Klebsiella microorganisms.

6. The method of claim 4 where the sample has a dissolved oxygen concentration and allowing the anaerobic microorganism to convert at least a portion of the nitroaromatic compound into a non-aromatic compound further comprises allowing the fermentative microorganism to ferment the carbohydrate, thereby lowering the dissolved oxygen concentration of at least a portion of the sample.

7. The method of claim 6 where lowering the oxygen concentration in at least a part of the sample comprises allowing fermentation by the fermentative microorganism to provide a redox potential of less than about −200 mV in at least a part of the sample.

8. The method of claim 1 where providing an anaerobic microorganism resistant to the nitroaromatic compound and capable of cleaving an aromatic ring of the nitroaromatic compound comprises providing within the sample a consortium of microorganisms that comprises the microorganism capable of cleaving the aromatic ring of the nitroaromatic compound.

9. The method of claim 1 further comprising the step of adding water to the sample.

10. The method of claim 8 where the sample is soil and the step of adding water to the sample thereby produces a soil slurry.

11. A method for converting a nitroaromatic compound in a sample into non-aromatic compounds, comprising:
    providing a sample comprising a nitroaromatic compound comprising a nitro group and an aromatic ring, the sample having a dissolved oxygen concentration;
    providing within the sample a consortium of microorganisms;
    reducing the dissolved oxygen concentration in the sample to a lower dissolved oxygen concentration; and
    allowing a microorganism of the consortium to convert the aromatic ring to a non-aromatic compound at the lower dissolved oxygen concentration.

12. The method of claim 11 further comprising providing within the sample a fermentative microorganism that is resistant to the nitroaromatic compound.

13. The method of claim 12 where the fermentative microorganism is selected from the group consisting of Klebsiella microorganisms.

14. The method of claim 12 further comprising adding a carbohydrate to the sample and providing within the sample effective conditions for fermentation of the carbohydrate by the carbohydrate-fermenting microorganism, thereby reducing the dissolved oxygen concentration of the sample to a concentration at which the anaerobic microorganism cleaves the aromatic ring of the nitroaromatic compound.

15. A method for converting a nitroaromatic compound in soil to a non-aromatic compound, comprising:
    providing a soil slurry comprising a nitroaromatic compound that comprises a nitro group and an aromatic ring, the soil slurry having a dissolved oxygen concentration;
    providing within the soil slurry a fermentative microorganism and an anaerobic microorganism capable of converting the aromatic ring of the nitroaromatic compound to a non-aromatic compound;
    providing within the soil slurry a nutrient supply comprising a carbohydrate;
    allowing the fermentative microorganism to ferment the carbohydrate, thereby producing a lower dissolved oxygen concentration in at least a portion of the soil slurry; and
    allowing the anaerobic microorganism to convert the aromatic ring of the nitroaromatic compound to a non-aromatic compound.

16. The method of claim 15 where producing a lower dissolved oxygen concentration comprises reducing the dissolved oxygen concentration in at least a portion of the soil slurry at least until a redox potential of −200 mV is provided.

17. The method of claim 15 where converting comprises cleaving the aromatic ring of the nitroaromatic compound.

18. The method of claim 15 where the nitroaromatic compound is selected from the group consisting of nitrophenols, nitrotoluenes, nitrocresols, nitrobenzoates, and mixtures thereof.

19. The method of claim 15, where the carbohydrate is a hydrolyzable polysaccharide.

20. The method of claim 15, where the anaerobic microorganism is a consortium of microorganisms comprising a Klebsiella microorganism.

* * * * *